United States Patent
Davies et al.

(10) Patent No.: US 7,534,793 B2
(45) Date of Patent: May 19, 2009

(54) AMINOPIPERIDINE QUINOLINES AND THEIR AZAISOSTERIC ANALOGUES WITH ANTIBACTERIAL ACTIVITY

(75) Inventors: David Thomas Davies, Harlow (GB); Graham Elgin Jones, Harlow (GB); Andrew P Lightfoot, Harlow (GB); Roger Edward Markwell, Harlow (GB); Neil David Pearson, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 23 days.

(21) Appl. No.: 11/219,148

(22) Filed: Sep. 2, 2005

(65) Prior Publication Data

US 2006/0014749 A1    Jan. 19, 2006

Related U.S. Application Data

(62) Division of application No. 10/333,829, filed on Aug. 28, 2003, now Pat. No. 6,962,917.

(51) Int. Cl.
    A61K 31/4709    (2006.01)
    C07D 215/16    (2006.01)

(52) U.S. Cl. ......................... 514/248; 514/312; 514/313; 546/153; 546/159

(58) Field of Classification Search .................. 546/153, 546/159; 514/312, 313
    See application file for complete search history.

(56) References Cited

U.S. PATENT DOCUMENTS

| | | | |
|---|---|---|---|
| 5,264,431 A | 11/1993 | Wacker et al. | 514/211 |
| 5,310,743 A | 5/1994 | Schilling et al. | 514/311 |
| 5,541,195 A | 7/1996 | Schilling et al. | 514/311 |
| 5,646,144 A | 7/1997 | Schilling et al. | 514/241 |
| 6,403,610 B1 | 6/2002 | Malleron et al. | 514/314 |
| 6,602,882 B1 | 8/2003 | Davies et al. | 514/300 |
| 6,602,884 B2 | 8/2003 | Bacque et al. | 514/314 |
| 6,603,005 B2 | 8/2003 | Bacque et al. | 546/176 |
| 6,815,547 B2 | 11/2004 | Bacque et al. | 546/174 |
| 6,903,217 B2 | 6/2005 | Bacque et al. | 546/180 |
| 6,911,442 B1 | 6/2005 | Davies et al. | 514/230.5 |
| 6,989,447 B2 | 1/2006 | Markwell et al. | 546/152 |
| 7,001,913 B1 | 2/2006 | Davies et al. | 514/300 |
| 2003/0212084 A1 | 11/2003 | Hatton et al. | 514/266.22 |
| 2004/0053928 A1 | 3/2004 | Davies et al. | 514/248 |
| 2004/0077655 A1 | 4/2004 | Dartois et al. | 514/253.05 |
| 2004/0077656 A1 | 4/2004 | Markwell et al. | 514/253.05 |
| 2004/0138219 A1 | 7/2004 | Davies et al. | 514/243 |
| 2004/0171620 A1 | 9/2004 | Brooks et al. | 514/248 |
| 2004/0198755 A1 | 10/2004 | Dartois et al. | 514/266.22 |

FOREIGN PATENT DOCUMENTS

| | | |
|---|---|---|
| CA | 2004986 A1 | 6/1990 |
| EP | 0238868 A2 | 9/1987 |
| EP | 0304493 A1 | 3/1989 |
| EP | 0 374 095 | 6/1990 |
| EP | 0532456 B1 | 3/1993 |
| EP | 0541486 A1 | 5/1993 |
| EP | 0823429 A1 | 2/1998 |
| EP | 1218370 B1 | 12/2004 |
| FR | 772190 | 1/1972 |
| GB | 1345872 | 2/1974 |
| GB | 1537867 | 1/1979 |
| JP | 07179407 | 7/1995 |
| JP | 1995179407 A | 7/1995 |
| WO | WO 95/09853 | 4/1995 |
| WO | WO 96/15128 | 5/1996 |
| WO | WO 96/38144 | 12/1996 |
| WO | WO 97/03069 | 1/1997 |
| WO | WO 97/17957 | 5/1997 |
| WO | WO 97/28167 | 8/1997 |
| WO | WO 97/45119 | 12/1997 |
| WO | WO 98/02438 | 1/1998 |
| WO | WO 99/37635 | 7/1999 |
| WO | WO 00/21948 | 4/2000 |
| WO | WO 00/21952 | 4/2000 |
| WO | WO 00/43383 | 7/2000 |
| WO | WO 00/78748 | 12/2000 |
| WO | WO 01/07432 | 2/2001 |
| WO | WO-01/07432 A1 * | 2/2001 |
| WO | WO 01/07433 | 2/2001 |
| WO | WO 01/25227 | 4/2001 |
| WO | WO 01/87839 | 11/2001 |
| WO | WO 02/07572 | 1/2002 |
| WO | WO 02/24684 A1 | 3/2002 |

(Continued)

OTHER PUBLICATIONS

U.S. Appl. No. 10/450,884, filed Nov. 13, 2003, Nadler et al.
U.S. Appl. No. 10/031,844, filed Jul. 12, 2002, Davies et al.
U.S. Appl. No. 09/600,984, filed Jan. 21, 1999, Quinoline Derivatives As Antibacterial, Warrack et al.

(Continued)

*Primary Examiner*—Kamal A. Saeed
*Assistant Examiner*—Janet L Coppins
(74) *Attorney, Agent, or Firm*—Loretta J. Sauermelch; Mary E. McCarthy; Charles M. Kinzig

(57) ABSTRACT

Aminopiperidine derivatives and pharmaceutically acceptable derivatives thereof useful in methods of treatment of bacterial infections in mammals, particularly in man

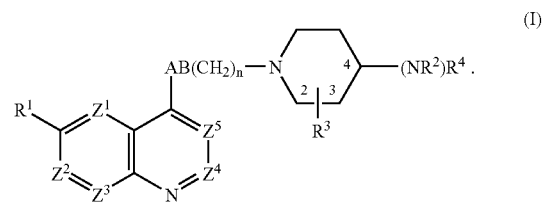

6 Claims, No Drawings

FOREIGN PATENT DOCUMENTS

| WO | WO 02/40474 | 5/2002 |
| WO | WO 02/50040 A1 | 6/2002 |
| WO | WO 02/50061 A1 | 6/2002 |
| WO | WO 02/56882 A1 | 7/2002 |
| WO | WO 02/072572 A1 | 9/2002 |
| WO | WO 02/096907 A1 | 12/2002 |
| WO | WO 03/087098 A1 | 10/2003 |

OTHER PUBLICATIONS

U.S. Appl. No. 10/032,403, filed Dec. 20, 2001, Naphthrydine Compounds and Their, Hatton et al.

U.S. Appl. No. 09/889/820, filed Jan. 17, 2000, Piperidinylquinolines As Protein Tyrosine Kinase Inhibitors, Davies et al.

U.S. Appl. No. 10/018,900, filed Jun. 13, 2000, Quinoline Derivatives As Antibacterials, Davies et al.

U.S. Appl. No. 10/720,788, filed Nov. 24, 2003, Compounds, Markwell et al.

U.S. Appl. No. 10/380,915, filed Sep. 4, 2003, Quinoline Derivatives As Antibacterials, Markwell et al.

U.S. Appl. No. 10/450,892, filed Nov. 13, 2003, Quinolines And Nitrogenated Derivatives Thereof Substituted, Pearson et al.

U.S. Appl. No. 10/466,394, filed Jan. 26, 2004, Substituted In 4-Position By A Piperidine-Containing Moiety And Their Use As Antibacterial Agents, Davies et al.

U.S. Appl. No. 10/477,900, filed May 24, 2002, Aromatic Ethyl Piperidine Antibacterials, Pearson et al.

U.S. Appl. No. 10/478,154, filed Apr. 6, 2004, Cyclohexane/Ene Antibacterials, Brooks et al.

\* cited by examiner

AMINOPIPERIDINE QUINOLINES AND THEIR AZAISOSTERIC ANALOGUES WITH ANTIBACTERIAL ACTIVITY

This application is a divisional application of U.S. Ser. No. 10/333,829 filed Aug. 28, 2003 now U.S. Pat. No. 6,962,917.

This invention relates to novel compounds, compositions containing them and their use as antibacterials.

WO99/37635, WO00/21948, WO00/21952, WO01/25227, WO00/43383, WO00/78748, WO01/07432 and WO01/07433 disclose piperidine and piperazine derivatives having antibacterial activity.

WO9717957 discloses piperidyl compounds which are haemoregulatory and stimulate haematopoesis. JP07179407 discloses piperidyl compounds which are useful for preventing thrombotic diseases, inhibiting tumour metastasis and accelerating wound healing.

We have now found a novel group of aminopiperidines which have antibacterial activity.

This invention provides a compound of formula (I) or a pharmaceutically acceptable derivative thereof:

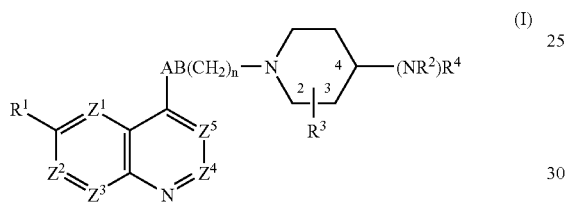

wherein:
one of $Z^1$, $Z^2$, $Z^3$, $Z^4$ and $Z^5$ is N, one is $CR^{1a}$ and the remainder are CH, or one or two of $Z^1$, $Z^2$, $Z^3$, $Z^4$ and $Z^5$ are independently $CR^{1a}$ and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino any of which is optionally N-substituted by one or two $(C_{1-6})$alkyl, acyl or $(C_{1-6})$alkylsulphonyl groups, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkoxy-substituted $(C_{1-6})$alkyl; halogen; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups; or when $Z^5$ is $CR^{1a}$, $R^{1a}$ may instead be cyano, hydroxymethyl or carboxy;

provided that when $Z^1$, $Z^2$, $Z^3$, $Z^4$ and $Z^5$ are $CR^{1a}$ or CH, then $R^1$ is not hydrogen;

$R^2$ is hydrogen, or $(C_{1-4})$alkyl or $(C_{2-4})$alkenyl optionally substituted with 1 to 3 groups selected from:
amino optionally substituted by one or two $(C_{1-4})$alkyl groups; carboxy; $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; halogen; $(C_{1-4})$alkylthio; trifluoromethyl; hydroxy optionally substituted by $(C_{1-4})$alkyl, $(C_{2-4})$alkenyl, $(C_{1-4})$alkoxycarbonyl, $(C_{1-4})$alkylcarbonyl, $(C_{2-4})$alkenyloxycarbonyl, $(C_{2-4})$alkenylcarbonyl; oxo; $(C_{1-4})$alkylsulphonyl; $(C_{2-4})$alkenylsulphonyl; or $(C_{1-4})$aminosulphonyl wherein the amino group is optionally substituted by $(C_{1-4})$alkyl or $(C_{2-4})$alkenyl;

$R^3$ is hydrogen; or $R^3$ is in the 2-, 3- or 4-position and is:
carboxy, $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the substituents listed above for $R^3$ and/or 0 to 2 groups $R^{12}$ independently selected from:
halogen; $(C_{1-6})$alkylthio; trifluoromethyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl; or when $R^3$ is in the 3-position, hydroxy optionally substituted as described above;

in addition when $R^3$ is disubstituted with a hydroxy or amino containing substituent and carboxy containing substituent these may together form a cyclic ester or amide linkage, respectively;

$R^4$ is a group —U—$R^5$ where

U is selected from CO, $SO_2$ and $CH_2$ and $R^5$ is an optionally substituted bicyclic carbocyclic or heterocyclic ring system (A):

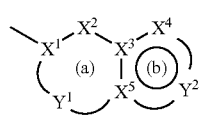

(A)

containing up to four heteroatoms in each ring in which ring (a) is aromatic or non aromatic;

$X^1$ is C when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^4$ is N, $NR^{13}$, O, $S(O)_x$, CO or $CR^{14}$;

$X^3$ and $X^5$ are independently N or C;

$Y^1$ is a 1 to 3 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 or 3 atom linker group completing an aromatic ring, each atom of $Y^2$ being independently selected from N, $NR^{13}$, O, $S(O)_x$, CO and $CR^{14}$;

each of $R^{14}$ and $R^{15}$ is independently selected from: H; $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl$(C_{1-4})$alkyl; hydroxy; hydroxy$(C_{1-4})$alkyl; mercapto $(C_{1-4})$alkyl; $(C_{1-4})$alkoxy, nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally mono- or di-substituted by $(C_{1-4})$alkyl or $(C_{2-4})$alkenyl; aryl; aryl$(C_{1-4})$alkyl; aryl$(C_{1-4})$alkoxy or $R^{14}$ and $R^{15}$ may together represent oxo;

each $R^{13}$ is independently H; trifluoromethyl; $(C_{1-4})$alkyl optionally substituted by hydroxy, $(C_{1-6})$alkoxy, $(C_{1-6})$alkylthio, carboxy, halo or trifluoromethyl; $(C_{2-4})$alkenyl; aryl; aryl $(C_{1-4})$alkyl; arylcarbonyl; heteroarylcarbonyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl;

n is 0 or 1;

each x is independently 0, 1 or 2

A is $NR^{11}$, O or $CR^6R^7$ and B is $NR^{11}$, O, $SO_2$ or $CR^8R^9$ and wherein:

each of $R^6$, $R^7$, $R^8$ and $R^9$ is independently selected from: hydrogen; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or aminosulphonyl wherein the amino group is optionally substituted by $(C_{1-6})$alkyl or $(C_{2-6})$alkenyl;

or when n=1 $R^6$ and $R^8$ together represent a bond and $R^7$ and $R^9$ are as above defined;

or $R^6$ and $R^7$ or $R^8$ and $R^9$ together represent oxo;

provided that:

when A is $NR^{11}$, B is not $NR^{11}$ or O;

when A is CO, B is not CO, O or $SO_2$;

when n is 0 and A is $NR^{11}$, $CR^8R^9$ can only be CO;

when A is $CR^6R^7$ and B is $SO_2$, n is 0;

when n is 0, B is not $NR^{11}$ or O or $R^8$ and $R^9$ are not optionally substituted hydroxy or amino;

when A is O, B is not $NR^{11}$, O, $SO_2$ or CO and n=1; and when A-B is $CR^7$=$CR^9$, n is 1

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl; and $(C_{2-6})$alkenylcarbonyl; and $R^{11}$ is hydrogen; trifluoromethyl, $(C_{1-6})$alkyl; $(C_{2-6})$alkenyl; $(C_{1-6})$alkoxycarbonyl; $(C_{1-6})$alkylcarbonyl; or aminocarbonyl wherein the amino group is optionally substituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl or $(C_{2-6})$alkenyl and optionally further substituted by $(C_{1-6})$alkyl or $(C_{2-6})$alkenyl;

or where one of $R^3$ and $R^6$, $R^7$, $R^8$ or $R^9$ contains a carboxy group and the other contains a hydroxy or amino group they may together form a cyclic ester or amide linkage.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

In one aspect, when U is $CH_2$, $R^5$ is not a heteroaryl group. In another aspect, when U is $CH_2$, R5 is not indolyl, quinolinyl or benzothienyl.

Preferably one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH.

Preferably $Z^5$ is CH or N, $Z^3$ is CH or CF and $Z^1$, $Z^2$ and $Z^4$ are each CH, or $Z^1$ is N, $Z^3$ is CH or CF and $Z^2$, $Z^4$ and $Z^5$ are each CH.

When $R^1$ or $R^{1a}$ is substituted alkoxy it is preferably $(C_{2-6})$alkoxy substitituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, amino $(C_{3-5})$alkyloxy, guanidino$(C_{3-5})$alkyloxy, piperidyl$(C_{3-5})$alkyloxy, nitro or fluoro; $R^1$ is more preferably methoxy, amino$(C_{3-5})$alkyloxy or guanidino$(C_{3-5})$alkyloxy. $R^{1a}$ is more preferably H or F. Most preferably $R^1$ is methoxy, and $R^{1a}$ is H or when $Z^3$ is $CR^{1a}$ it may be C—F.

When $Z^5$ is $CR^{1a}$, $R^{1a}$ is preferably hydrogen, cyano, hydroxymethyl or carboxy, most preferably hydrogen.

Preferably n is 0.

$R^2$ is preferably hydrogen; $(C_{1-4})$alkyl substituted with carboxy, optionally substituted hydroxy, optionally substituted aminocarbonyl, optionally substituted amino or $(C_{1-4})$ alkoxycarbonyl; or $(C_{2-4})$alkenyl substituted with $(C_{1-4})$ alkoxycarbonyl or carboxy. More preferred groups for $R^2$ are hydrogen, carboxymethyl, hydroxyethyl, aminocarbonylmethyl, ethoxycarbonylmethyl, ethoxycarbonylallyl and carboxyallyl, most preferably hydrogen.

Preferred examples of $R^3$ include hydrogen; optionally substituted hydroxy; $(C_{1-4})$ alkyl; ethenyl; optionally substituted 1-hydroxy-$(C_{1-4})$ alkyl; optionally substituted aminocarbonyl; carboxy$(C_{1-4})$alkyl; optionally substituted aminocarbonyl$(C_{1-4})$alkyl; cyano$(C_{1-4})$alkyl; optionally substituted 2-oxo-oxazolidinyl and optionally substituted 2-oxo-oxazolidinyl$(C_{1-4}$alkyl). More preferred $R^3$ groups are hydrogen; $CONH_2$; 1-hydroxyalkyl e.g. $CH_2OH$, $CH(OH)$ $CH_2CN$; $CH_2CO_2H$; $CH_2CONH_2$; —$CONHCH_2CONH_2$; 1,2-dihydroxyalkyl e.g. $CH(OH)CH_2OH$; $CH_2CN$; 2-oxo-oxazolidin-5-yl and 2-oxo-oxazolidin-5-yl$(C_{1-4}$alkyl). Most preferably $R^3$ is hydrogen.

$R^3$ is preferably in the 3- or 4-position.

When $R^3$ and $R^6$, $R^7$, $R^8$ or $R^9$ together form a cyclic ester or amide linkage, it is preferred that the resulting ring is 5-7 membered. It is further preferred that the group A or B which does not form the ester or amide linkage is $CH_2$.

When A is CH(OH) the R-stereochemistry is preferred.

Preferably A is NH, $NCH_3$, $CH_2$, CHOH, $CH(NH_2)$, $C(Me)(OH)$ or CH(Me).

Preferably B is $CH_2$ or CO.

Preferably A-B is CHOH—$CH_2$, $NR^{11}$—$CH_2$ or $NR^{11}$—CO.

Particularly preferred are those compounds where n=0, A is NH and B is CO, or A is CHOH and B is $CH_2$, when more preferably A is the R-isomer of CHOH.

Preferably $R^{11}$ is hydrogen or $(C_{1-4})$alkyl e.g. methyl, more preferably hydrogen.

U is most preferably $CH_2$.

Preferably $R^5$ is an aromatic heterocyclic ring (A) having 1-4 heteroatoms of which one is N or $NR^{13}$.

Examples of Rings (A) Include Optionally Substituted:

(a) and (b) Aromatic 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2-yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimidin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thiazolo[5,4-b]pyridin-6-yl, thieno[3,2-b]pyridin-6-yl, 2H-isoquinolin-1-one-3-yl.

(a) is Non Aromatic (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-(2,3-dihydro-[1,4]dioxino[2,3-b]pyridin-3-yl, 2,3-dihydro-[1,4]dioxino[2,3-b]pyridin-3-yl, and 3-substituted-3H-quinazolin-4-one-2-yl.

In one aspect, when $R^{13}$ is optionally substituted $(C_{1-4})$ alkyl, the optional substituent is other than carboxy.

$R^{13}$ is preferably H if in ring (a) or in addition $(C_{1-4})$alkyl such as methyl or isopropyl when in ring (b). More preferably, in ring (b) $R^{13}$ is hydrogen when $NR^{13}$ is bonded to $X^3$ and $(C_{1-4})$alkyl when $NR^{13}$ is bonded to $X^5$.

$R^{14}$ and $R^{15}$ are preferably independently selected from hydrogen, halo, hydroxy, $(C_{1-4})$allyl, $(C_{1-4})$alkoxy, trifluoromethoxy, nitro, cyano, aryl$(C_{1-4})$alkoxy and $(C_{1-4})$alkylsulphonyl. More preferably $R^{15}$ is hydrogen.

More preferably each $R^{14}$ is selected from hydrogen, chloro, fluoro, hydroxy, methyl, methoxy, trifluoromethoxy, benzyloxy, nitro, cyano and methylsulphonyl. Most preferably $R^{14}$ is selected from hydrogen, hydroxy, fluorine or nitro. Preferably 0-3 groups $R^{14}$ are substituents other than hydrogen. Preferably when $R^{14}$ is not hydrogen, $X^4$ is $CR^{14}$ and/or $CR^{14}$ is a component of $Y^2$.

Most preferred groups $R^5$ include 4,6-difluoro-indol-2-yl, 1H-pyrrolo[2,3-b]-pyridin-2-yl, 1H-pyrrolo[3,2-b]-pyridin-2-yl, 8-hydroxy-quinolin-2-yl, quinoxalin-2-yl, benzimidazol-2-yl, benzo[1,2,3]-thiadiazol-5-yl, benzothiophen-2-yl, 4,6-difluoro-1H-benzimidazol-2-yl, benzothiazole-5-yl and 3-(R)-2,3-dihydro-[1,4]dioxino[2,3-b]pyridin-3-yl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term 'alkenyl' should be interpreted accordingly.

Halo or halogen includes fluoro, chloro, bromo and iodo.

Haloalkyl moieties include 1-3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$ alkylthio; halo; carboxy$(C_{1-4})$allyl; halo$(C_{1-4})$alkoxy; halo $(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$ alkoxycarbonyl$(C_{1-4})$alkyl; hydroxy, hydroxy$(C_{1-4})$alkyl; mercapto$(C_{1-4})$alkyl; $(C_{1-4})$alkoxy, nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl$(C_{1-4})$ alkoxy and oxo groups.

Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; carboxy$(C_{1-4})$alkyl; halo$(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl $(C_{1-4})$alkyl; hydroxy; hydroxy$(C_{1-4})$aklyl; mercapto$(C_{1-4})$alkyl; $(C_{1-4})$alkoxy; nitro; cyano; carboxy, amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy The term "acyl" includes formyl and $(C_{1-6})$alkylcarbonyl group.

Preferred compounds of formula (I) include:
(R)-2-{4-[(4-fluoro-1H-benzimidazol-2-ylmethyl)-amino]-piperidin-1-yl}-1-(6-methoxyquinolin-4-yl)-ethanol;
(R)-1-(6-methoxy-quinolin-4-yl)-2-{4-[(1H-pyrrolo[2,3-b]pyridine-2-ylmethyl)-amino]-piperidin-1-yl}-ethanol;
2-({1-[(R)-2-hydroxy-2-(6-methoxy-quinolin-4-yl)-ethyl]-piperidin-4-ylamino}-methyl)-quinolin-8-ol;
(R)-2-{4-[(benzo[1,2,3]thiadiazol-5-ylmethyl)-amino]-piperidin-1-yl}-1-(6-methoxy-quinolin-4-yl)-ethanol;
(R)-1-(6-methoxy-quinolin-4-yl)-2-{4-[(quinoxalin-2-ylmethyl)-amino]-piperidin-1-yl}-ethanol;
2-({1-[(R)-2-hydroxy-2-(6-methoxy-[1,5]naphthyridin-4-yl)-ethyl]-piperidin-4-ylamino}-methyl)-quinolin-8-ol;
4-[(4,7-difluoro-1H-indol-2-ylmethyl)-amino]-piperidine-1carboxylic acid (6-methoxy-[1,5]naphthyridin-4-yl)-amide;
(R)-2-(4-{[(R)-1-(2,3-Dihydro-[1,4]dioxino[2,3-]pyridin-3-yl)methyl]-amino}-piperidin-1-yl)-1-(8-fluoro-6-methoxy-quinolin-4-yl)-ethanol;
(R)-2-{4-[(Benzothiazol-5-ylmethyl)-amino]-piperidin-1-yl}-1-(6-methoxy-quinolin-4-yl)-ethanol; and
(R)-2-{4-[(4,6-Difluoro-1H-benzimidazol-2-ylmethyl)-amino]-piperidin-1-yl}-1-(6-methoxy[1,5]naphthyridin-4-yl)-ethanol;

and pharmaceutically acceptable derivatives thereof.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

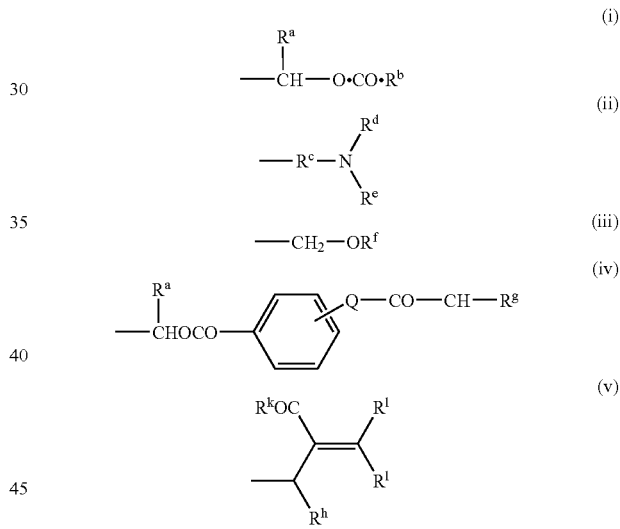

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; ($C_{1-6}$)alkoxycarbonyloxy($C_{1-6}$)alkyl groups, such as ethoxycarbonyloxymethyl, α-ethoxycarbonyloxyethyl and propoxycarbonyloxyethyl; di($C_{1-6}$)alkylamino($C_{1-6}$)alkyl especially di($C_{1-4}$)alkylamino ($C_{1-4}$)alkyl groups such as dimethylaminomethyl, dimethylaminoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

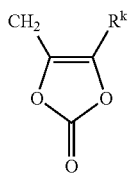

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group CH(OH)—$CH_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises:

reacting a compound of formula (IV) with a compound of formula (V):

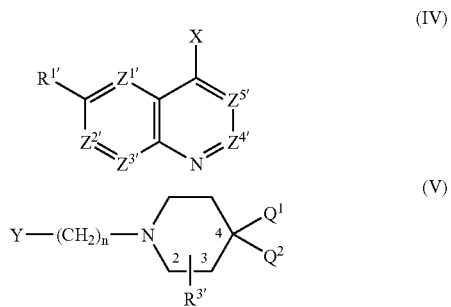

wherein n is as defined in formula (I); $Z^{1'}, Z^{2'}, Z^{3'}, Z^{4'}, Z^{5'}, R^{1'}$ and $R^{3'}$ are $Z^1, Z^2, Z^3, Z^4, Z^5, R^1$ and $R^3$ as defined in formula (I) or groups convertible thereto;

$Q^1$ is $NR^{2'}R^{4'}$ or a group convertible thereto wherein $R^{2'}$ and $R^{4'}$ are $R^2$ and $R^4$ as defined in formula (I) or groups convertible thereto and $Q^2$ is H or $R^{3'}$ or $Q^1$ and $Q^2$ together form an optionally protected oxo group;

and X and Y may be the following combinations:
(i) X is A'-COW, Y is H and n is 0;
(ii) X is $CR^6$=$CR^8R^9$, Y is H and n is 0;
(iii) X is oxirane, Y is H and n is 0;
(iv) X is N=C=O and Y is H and n is 0;
(v) one of X and Y is $CO_2R^y$ and the other is $CH_2CO_2R^x$;
(vi) X is $CHR^6R^7$ and Y is C(=O)$R^9$;
(vii) X is $CR^7$=$PR^z_3$ and Y is C(=O)$R^9$ and n=1;
(viii) X is C(=O)$R^7$ and Y is $CR^9$=$PR^z_3$ and n=1;
(ix) Y is COW and X is $NHR^{11'}$, or $NR^{11'}$COW and n=0 or 1 or when n−1 X is COW and Y is $NHR^{11'}$, or $NR^{11'}$COW;
(x) X is C(O=)$R^6$ and Y is $NHR^{11'}$ or X is $NHR^{11'}$ and Y is C(=O)$R^8$ and n=1;
(xi) X is $NHR^{11'}$ and Y is $CR^8R^9W$ and n=1;
(xii) X is $CR^6R^7W$ and Y is $NHR^{11'}$ or OH and n=1;
(xiii) X is $CR^6R^7SO_2W$ and Y is H and n=0;
(xiv) X is W or OH and Y is $CH_2OH$ and n=1;
(xv) X is $NHR^{11'}$ and Y is $SO_2W$ or X is $NR^{11'}SO_2W$ and Y is H, and n=0;
(xvi) X is $NR^{11'}COCH_2W$ or $NR^{11'}SO_2CH_2W$ and Y is H and n=0;
(xvii) X is W and Y is $CONHR^{11'}$;

in which W is a leaving group, e.g. halo or imidazolyl; $R^x$ and $R^y$ are ($C_{1-6}$)alkyl; $R^z$ is aryl or ($C_{1-6}$)alkyl; A' and $NR^{11'}$ are A and $NR^{11}$ as defined in formula (I), or groups convertible thereto; and oxirane is:

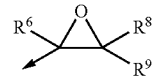

wherein $R^6$, $R^8$ and $R^9$ are as defined in formula (I);

and thereafter optionally or as necessary converting $Q^1$ and $Q^2$ to $NR^{2'}R^{4'}$; converting A', $Z^{1'}, Z^{2'}, Z^{3'}, Z^{4'}, Z^{5'}, R^{1'}, R^{2'}, R^{3'}, R^{4'}$ and $NR^{11'}$ to A, $Z^1, Z^2, Z^3, Z^4, Z^5, R^1, R^2, R^3, R^4$ and $NR^{11}$; converting A-B to other A-B, interconverting $R^1, R^2, R^3$ and/or $R^4$, and/or forming a pharmaceutically acceptable derivative thereof.

Process variant (i) initially produces compounds of formula (I) wherein A-B is A'-CO.

Process variant (ii) initially produces compounds of formula (I) wherein A-B is $CHR^6$—$CR^8R^9$.

Process variant (iii) initially produces compounds of formula (I) wherein A-B is $CR^6$(OH)—$CR^8R^9$.

Process variant (iv) initially produces compounds of formula (I) where A-B is NH—CO.

Process variant (v) initially produces compounds of formula (I) wherein A-B is CO—$CH_2$ or $CH_2$—CO.

Process variant (vi) initially produces compounds of formula (I) wherein A-B is $CR^6R^7$—$CR^9OH$.

Process variant (vii) and (viii) initially produce compounds of formula (I) wherein A-B is $CR^7$=$CR^9$.

Process variant (ix) initially produces compounds of formula (I) where A-B is CO—$NR^{11}$ or $NR^{11}$—CO.

Process variant (x) initially produces compounds of formula (I) wherein A-B is $CHR^6$—$NR^{11}$ or $NR^{11}$—$CHR^8$.

Process variant (xi) initially produces compounds of formula (I) wherein A-B is $NR^{11'}$—$CR^8R^9$.

Process variant (xii) initially produces compounds of formula (I) wherein A-B is $CR^6R^7$—$NR^{11'}$ or $CR^6R^7$—O.

Process variant (xiii) initially produces compounds of formula (I) where A-B is $CR^6R^7$—$SO_2$.

Process variant (xiv) initially produces compounds of formula (I) wherein A-B is O—$CH_2$.

Process variant (xv) initially produces compounds where AB is $NR^{11}SO_2$.

Process variant (xvi) initially produces compounds of formula (I) where A-B is $NR^{11'''}$—CO or $NR^{11'}$—$SO_2$ and n=1.

Process variant (xvii) initially produces compounds of formula (I) where A-B is $NR^{11'}$—CO.

In process variants (i) and (ix) the reaction is a standard amide or urea formation reaction involving e.g.:
1. Activation of a carboxylic acid (e.g. to an acid chloride, mixed anhydride, active ester, O-acyl-isourea or other species), and treatment with an amine (Ogliaruso, M. A.; Wolfe, J. F. in *The Chemistry of Functional Groups (Ed. Patai, S.) Suppl. B: The Chemistry of Acid Derivatives, Pt.* 1 (John Wiley and Sons, 1979), pp 442-8; Beckwith, A. L. J. in *The Chemistry of Functional Groups (Ed. Patai, S)Suppl. B: The Chemistry of Amides (Ed. Zabricky, J.)* (John Wiley and Sons, 1970), p 73 ff. The acid and amide are preferably reacted in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N'N'-tetramethyluronium hexafluorophosphate (HATU); or
2. The specific methods of:
a. in situ conversion of an acid into the amine component by a modified Curtius reaction procedure (Shioiri, T., Murata, M., Hamada, Y., *Chem. Pharm. Bull.* 1987, 35, 2698)
b. in situ conversion of the acid component into the acid chloride under neutral conditions (Villeneuve, G. B.; Chan, T. H., *Tetrahedron. Lett.* 1997, 38, 6489).

A' may be, for example protected hydroxymethylene.

The process variant (ii) is a standard addition reaction using methods well known to those skilled in the art. The process is preferably carried out in a polar organic solvent e.g. acetonitrile in the presence of an organic base e.g. triethylamine.

In process variant (iii) the coupling may be effected in acetonitrile at room temperature in the presence of one equivalent of lithium perchlorate as catalyst (general method of J. E. Chateauneuf et al, *J. Org. Chem.*, 56, 5939-5942, 1991) or more preferably with ytterbium triflate in dichloromethane. In some cases an elevated temperature such as 40-70° C. may be beneficial. Alternatively, the piperidine may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

The process variant (iv) is a standard urea formation reaction from the reaction of an isocyanate with an amine and is conducted by methods well known to those skilled in the art (for example see March, J; *Advanced Organic Chemistry, Edition* 3 (John Wiley and Sons, 1985), p 802-3). The process is preferably carried out in a polar solvent such as N,N-dimethylformamide.

In process variant (v) the process is two step: firstly a condensation using a base, preferably sodium hydride or alkoxide, sodamide, alkyl lithium or lithium dialkylamide, preferably in an aprotic solvent e.g. ether, THF or benzene; secondly, hydrolysis using an inorganic acid, preferably HCl in aqueous organic solvent at 0-100° C. Analogous routes are described in DE330945, EP31753, EP53964 and H. Sargent, J. Am. Chem. Soc. 68, 2688-2692 (1946). Similar Claisen methodology is described in Soszko et. al., Pr. Kom. Mat. Przyr. Poznan. Tow. Przyj. Nauk., (1962), 10, 15.

In process variant (vi) the reaction is carried out in the presence of a base, preferably organometallic or metal hydride e.g. NaH, lithium diisopropylamide or NaOEt, preferably in an aprotic solvent, preferably THF, ether or benzene at −78 to 25° C. (analogous process in Gutswiller et al. (1978) J. Am. Chem. Soc. 100, 576).

In process variants (vii) and (viii) if a base is used it is preferably NaH, KH, an alkyl lithium e.g. BuLi, a metal alkoxide e.g. NaOEt, sodamide or lithium dialkylamide e.g. di-isopropylamide. An analogous method is described in U.S. Pat. No. 3,989,691 and M. Gates et. al. (1970) J. Amer. Chem. Soc., 92, 205, as well as Taylor et al. (1972) JACS 94, 6218.

In process variant (x) where X or Y is CHO the reaction is a standard reductive alkylation using, e.g., sodium borohydride or sodium triacetoxyborohydride (Gribble, G. W. in *Encyclopedia of Reagents for Organic Synthesis* (Ed. Paquette, L. A) (John Wiley and Sons, 1995), p 4649).

The process variants (xi) and (xii) are standard alkylation reactions well known to those skilled in the art, for example where an alcohol or amine is treated with an alkyl halide in the presence of a base (for example see March, J; *Advanced Organic Chemistry, Edition* 3 (John Wiley and Sons, 1985), p 364-366 and p 342-343). The process is preferably carried out in a polar solvent such as N,N-dimethylformamide In process variant (xiii) the reaction is a standard sulphonamide formation reaction well known to those skilled in the art. This may be e.g. the reaction of a sulphonyl halide with an amine.

In process variant (xiv) where X is W such as halogen, methanesulphonyloxy or trifluoromethanesulphonyloxy, the hydroxy group in Y is preferably converted to an OM group where M is an alkali metal by treatment of an alcohol with a base. The base is preferably inorganic such as NaH, lithium diisopropylamide or sodium. Where X is OH, the hydroxy group in Y is activated under Mitsunobu conditions (Fletcher et. al. J Chem Soc. (1995), 623). Alternatively the X=O and Y=$CH_2OH$ groups can be reacted directly by activation with dichlorocarbodiimide (DCC) (Chem. Berichte 1962, 95, 2997 or Angewante Chemie 1963 75, 377).

In process variant (xv) the reaction is conducted in the presence of an organic base such as triethylamine or pyridine such as described by Fuhrman et. al., J. Amer. Chem. Soc.; 67, 1245, 1945. The X=$NR^{11'}SO_2W$ or Y=$SO_2W$ intermediates can be formed from the requisite amine e.g. by reaction with $SO_2Cl_2$ analogously to the procedure described by the same authors Fuhrman et. al., J. Amer. Chem. Soc.; 67, 1245, 1945.

In process variant (xvi) the reaction is an alkylation, examples of which are described in J. Med. chem. (1979) 22(10) 1171-6. The compound of formula (IV) may be prepared from the corresponding compound where X is $NHR^{11'}$ by acylation with an appropriate derivative of the acid $WCH_2COOH$ such as the acid chloride or sulphonation with an appropriate derivative of the sulphonic acid $WCH_2SO_3H$ such as the sulphonyl chloride.

In process variant (xvii) the leaving group W is preferably chloro or trifluoromethylsulphonyl and the reaction is the palladium catalysed process known as the "Buchwald" reaction (J. Yin and S. L. Buchwald, Org. Lett., 2000, 2, 1101).

Reduction of a carbonyl group A or B to CHOH can be readily accomplished using reducing agents well known to those skilled in the art, e.g. sodium borohydride in aqueous ethanol or lithium aluminium hydride in ethereal solution. This is analogous to methods described in EP53964, U.S. Pat. No. 384,556 and J. Gutzwiller et al, *J. Amer. Chem. Soc.*, 1978, 100, 576.

The carbonyl group A or B may be reduced to $CH_2$ by treatment with a reducing agent such as hydrazine in ethylene glycol, at e.g. 130-160° C., in the presence of potassium hydroxide.

Reaction of a carbonyl group A or B with an organometallic reagent yields a group where $R^8$ is OH and $R^9$ is alkyl.

A hydroxy group on A or B may be oxidised to a carbonyl group by oxidants well known to those skilled in the art, for example, manganese dioxide, pyridinium chlorochromate or pyridinium dichromate.

A hydroxyalkyl A-B group $CHR^7CR^9OH$ or $CR^7(OH)CHR^9$ may be dehydrated to give the group $CR^7=CR^9$ by treatment with an acid anhydride such as acetic anhydride.

Methods for conversion of $CR^7=CR^9$ by reduction to $CHR^7CHR^9$ are well known to those skilled in the art, for example using hydrogenation over palladium on carbon as catalyst. Methods for conversion of $CR^7=CR^9$ to give the A-B group $CR^7(OH)CHR^9$ or $CHR^7CR^9OH$ are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A or B may be converted to azido by activation and displacement e.g. under Mitsunobu conditions using hydrazoic acid or by treatment with diphenylphosphorylazide and base, and the azido group in turn may be reduced to amino by hydrogenation.

An example of a group $Q^1$ convertible to $NR^2R^4$ is $NR^{2'}R^{4'}$ or halogen. Halogen may be displaced by an amine $HNR^{2'}R^{4'}$ by a conventional alkylation.

When $Q^1 Q^2$ together form a protected oxo group this may be an acetal such as ethylenedioxy which can subsequently be removed by acid treatment to give a compound of formula (VI):

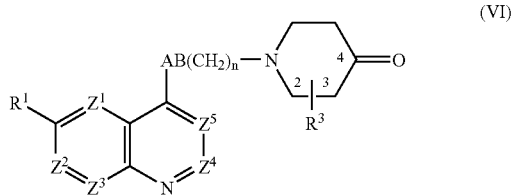

(VI)

wherein the variables are as described for formula (I)

Intermediates of formula (VI) are novel and as such form part of the invention.

The ketone of formula (VI) is reacted with an amine $HNR^{2'}R^{4'}$ by conventional reductive alkylation as described above for process variant (x).

Examples of groups $Z^{1'}, Z^{2'}, Z^{3'}, Z^{4'}, Z^{5'}$ convertible to $Z^1, Z^2, Z^3, Z^4$ and $Z^5$ include $CR^{1a'}$ where $R^{1a'}$ is a group convertible to $R^{1a}$. $Z^{1'}, Z^{2'}, Z^{3'}, Z^{4'}$ and $Z^{5'}$ are preferably $Z^1, Z^2, Z^3, Z^4$ and $Z^5$.

$R^{1a'}, R^{1'}$ and $R^{2'}$ are preferably $R^{1a}, R^1$ and $R^2$. $R^{1'}$ is preferably methoxy. $R^{2'}$ is preferably hydrogen. $R^{3'}$ is $R^3$ or more preferably hydrogen, vinyl, alkoxycarbonyl or carboxy. $R^{4'}$ is $R^4$ or more preferably H or an N-protecting group such as t-butoxycarbonyl, benzyloxycarbonyl or 9-fluorenylmethyloxycarbonyl.

Conversions of $R^1, R^{2'}, R^3$ and $R^4$ and interconversions of $R^1, R^2, R^3$ and $R^4$ are conventional. In compounds which contain an optionally protected hydroxy group, suitable conventional hydroxy protecting groups which may be removed without disrupting the remainder of the molecule include acyl and alkylsilyl groups. N-protecting groups are removed by conventional methods.

For example $R^{1'}$ methoxy is convertible to $R^{1'}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1]nonane, epoxidation and reduction or oxymercuration.

$R^3$ 1,2-dihydroxyalkyl can be prepared from $R^{3'}$ alkenyl using osmium tetroxide or other reagents well known to those skilled in the art (see Advanced Organic Chemistry, Ed. March, J., John Wiley and Sons, 1985, p 732-737 and refs. cited therein) or epoxidation followed by hydrolysis (see Advanced Organic Chemistry, Ed. March, J. John Wiley and Sons, 1985, p 332, 333 and refs. cited therein).

$R^3$ vinyl can be chain extended by standard homologation, e.g. by conversion to hydroxyethyl followed by oxidation to the aldehyde, which is then subjected to a Wittig reaction.

Opening an epoxide-containing $R^{3'}$ group with cyanide anion yields a $CH(OH)—CH_2CN$ group.

Opening an epoxide-containing $R^{3'}$ group with azide anion yields an α-hydroxy azide derivative which can be reduced to the α-hydroxy amine. Conversion of the α-hydroxy amine to a carbamate is followed by ring closure with base to give the 2-oxo-oxazolidinyl containing $R^3$ group.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, *Ann. Chem.*, 1985, 1817; Rozenberg et al, *Angew. Chem. Int. Ed. Engl.*, 1994, 33(1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in water/methanol (E. R. H. Jones et al, *J. Chem. Soc.*, 1946, 39). Other oxidising agents may be used for this transformation such as sodium periodate catalysed by ruthenium trichloride (G. F. Tutwiler et al, *J. Med. Chem.*, 1987, 30(6), 1094), chromium trioxide-pyridine (G. Just et al, *Synth. Commun.*, 1979, 9(7). 613), potassium permanganate (D. E. Reedich et al, *J. Org. Chem.*, 1985, 50(19), 3535), and pyridinium chlorochromate (D. Askin et al, *Tetrahedron Lett.*, 1988, 29(3, 277).

The carboxy group may alternatively be formed in a two stage process, with an initial oxidation of the alcohol to the corresponding aldehyde using for instance dimethyl sulphoxide activated with oxalyl chloride (N. Cohen et al, J. Am. Chem. Soc., 1983, 105, 3661) or dicyclohexylcarbodiimide (R. M. Wengler, Angew. Chim. Int. Ed. Eng., 1985, 24(2), 77), or oxidation with tetrapropylammonium perruthenate (Ley et al, J. Chem. Soc. Chem Commun., 1987, 1625). The aldehyde may then be separately oxidised to the corresponding acid using oxidising agents such as silver (II) oxide (R. Grigg et al, J. Chem. Soc. Perkin1, 1983, 1929), potassium permanganate (A. Zurcher, Helv. Chim. Acta., 1987, 70 (7), 1937), sodium periodate catalysed by ruthenium trichloride (T. Sakata et al, Bull. Chem. Soc. Jpn., 1988, 61(6), 2025), pyridinium chlorochromate (R. S. Reddy et al, Synth. Commun., 1988, 18(51), 545) or chromium trioxide (R. M. Coates et al, *J. Am. Chem. Soc.*, 1982, 104, 2198).

An $R^3$ $CO_2H$ group may also be prepared from oxidative cleavage of the corresponding diol, $CH(OH)CH_2OH$, using sodium periodate catalysed by ruthenium trichloride with an acetontrile-carbontetrachloride-water solvent system (V. S. Martin et al, *Tetrahedron Letters*, 1988, 29(22), 2701).

Other routes to the synthesis of carboxy groups within $R^3$ are well known to those skilled in the art.

$R^3$ groups containing a cyano or carboxy group may be prepared by conversion of an alcohol to a suitable leaving group such as the corresponding tosylate by reaction with para-toluenesulphonyl chloride (M. R. Bell, *J. Med. Chem.*, 1970, 13, 389), or the iodide using triphenylphosphine, iodine, and imidazole (G. Lange, *Synth. Commun.*, 1990, 20, 1473). The second stage is the displacement of the leaving group with cyanide anion (L. A. Paquette et al, *J. Org. Chem.*, 1979, 44(25) 4603; P. A. Grieco et al, *J. Org. Chem.*, 1988, 53(16), 3658. Finally acidic hydrolysis of the nitrile group gives the desired acids (H. Rosemeyer et al, *Heterocycles*, 1985, 23 (10), 2669). The hydrolysis may also be carried out with base e.g. potassium hydroxide (H. Rapoport, J. Org. Chem., 1958, 23, 248) or enzymatically (T. Beard et al, *Tetrahedron Asymmetry*, 1993, 4 (6), 1085).

Other functional groups in $R^3$ may be obtained by conventional conversions of carboxy or cyano groups.

Tetrazoles are conveniently prepared by reaction of sodium azide with the cyano group (e.g. F. Thomas et al, *Bioorg. Med. Chem. Lett.*, 1996, 6(6), 631; K. Kubo et al, *J. Med. Chem.*, 1993, 3, 2182) or by reaction of azidotri-n-butyl stannane with the cyano group followed by acidic hydrolysis (P. L. Ornstein, *J. Org. Chem.*, 1994, 59, 7682 and *J. Med. Chem,* 1996, 39 (11), 2219).

The 3-hydroxy-3-cyclobutene-1,2-dion-4-yl group (e.g. R. M. Solt, *Bioorg. Med. Chem. Lett.*, 1993, 3(4), 757 and W. A. Kinney, *J. Med. Chem.*, 1992, 35(25), 4720) can be prepared by the following sequence:—(1) a compound where $R^3$ is $(CH_2)_nCHO$ (n=0, 1, 2) is treated with triethylamine, carbon tetrabromide-triphenylphosphine to give initially $(CH_2)_n$ CH=CHBr; (2) dehydrobromination of this intermediate to give the corresponding bromoethyne derivative $(CH_2)_n$ C≡CBr (for this 2 stage sequence see D. Grandjean et al, *Tetrahedron Lett.*, 1994, 35(21), 3529); (3) palladium-catalysed coupling of the bromoethyne with 4-(1-methylethoxy)-3-(tri-n-butylstannyl)cyclobut-3-ene-1,2-dione (Liebeskind et al, *J. Org. Chem.*, 1990, 55, 5359); (4) reduction of the ethyne moiety to —$CH_2CH_2$— under standard conditions of hydrogen and palladium on charcoal catalysis (see Howard et al, *Tetrahedron*, 1980, 36, 171); and finally (4) acidic hydrolysis of the methyl ethoxyester to generate the corresponding 3-hydroxy-3-cyclobutene-1,2-dione group (R. M. Soll, *Bioorg. Med. Chem. Lett.*, 1993, 3(4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, *J. Med Chem*, 1996, 39(11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, *J. Med. Chem.*, 1996, 39(11), 2232).

The hydroxamic acid groups are prepared from the corresponding acids by standard amide coupling reactions e.g. N. R. Patel et al, *Tetrahedron*, 1987, 43(22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is decribed by Y. Kohara et al, *Bioorg. Med. Chem. Lett.*, 1995, 5(17), 1903.

1,2,4-Triazol-5-yl groups may be prepared from the corresponding nitrile by reaction with an alcohol under acid conditions followed by reaction with hydrazine and then an $R^{10}$-substituted activated carboxylic acid (see J. B. Polya in "Comprehensive Heterocyclic Chemistry" Edition 1, p 762, Ed A. R. Katritzky and C. W. Rees, Pergamon Press, Oxford, 1984 and J. J. Ares et al, *J. Heterocyclic Chem.*, 1991, 28(5), 1197).

Other substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate. A carboxylate group may be converted to a hydroxymethyl group by reduction of an ester of this acid with a suitable reducing agent such as $LiAlH_4$.

An $NH_2$ substituent on piperidine is converted to $NR^2R^4$ by conventional means such as amide or sulphonamide formation with an acyl derivative $R^5COW$ or $R^5SO_2W$, for compounds where U is CO or $SO_2$ or, where U is $CH_2$, alkylation with an alkyl halide $R^5CH_2$-halide in the presence of base, acylation/reduction with an acyl derivative $R^5COW$ or reductive alkylation with an aldehyde $R^5CHO$.

Where one of $R^3$ and $R^6$, $R^7$, $R^8$ or $R^9$ contains a carboxy group and the other contains a hydroxy or amino group they may together form a cyclic ester or amide linkage. This linkage may form spontaneously during coupling of the compound of formula (IV) and the piperidine moiety or in the presence of standard peptide coupling agents.

It will be appreciated that under certain circumstances interconversions may interfere, for example, A or B hydroxy groups in A or B and the piperidine substituent $NH_2$ will require protection e.g. as a carboxy- or silyl-ester group for hydroxy and as an acyl derivative for piperidine $NH_2$, during conversion of $R^{1'}$, $R^{2'}$, $R^{3'}$ or $R^{4'}$, or during the coupling of the compounds of formulae (IV) and (V).

Compounds of formulae (IV) and (V) are known compounds, (see for example Smith et al, *J. Amer. Chem. Soc.*, 1946, 68, 1301) or prepared analogously.

Compounds of formula (IV) where X is $CR^6R^7SO_2W$ may be prepared by a route analogous to that of Ahmed El Hadri et al, *J. Heterocyclic Chem.*, 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

The isocyanate of formula (IV) may be prepared conventionally from a 4-amino derivative such as 4-aminoquinoline, and phosgene, or phosgene equivalent (eg triphosgene) or it may be prepared more conveniently from a 4-carboxylic acid by a "one-pot" Curtius Reaction with diphenyl phosphoryl azide (DPPA) [see T. Shiori et al. *Chem. Pharm. Bull.* 35, 2698-2704 (1987)].

The 4-amino derivatives are commercially available or may be prepared by conventional procedures from a corresponding 4-chloro or 4-trifluoromethanesulphonate derivative by treatment with ammonia (O. G. Backeberg et. al., J. Chem Soc., 381, 1942) or propylamine hydrochloride (R. Radinov et. al., Synthesis, 886, 1986).

4-Alkenyl compounds of formula (IV) may be prepared by conventional procedures from a corresponding 4-halogeno-derivative by e.g. a Heck synthesis as described in e.g. *Organic Reactions,* 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in *Heterocyclic Compounds,* 6, 324 (1957) Ed. R. C. Elderfield.

Activated carboxy derivatives X=A'COW of formula (IV) may be prepared from X=A'CO$_2$H derivatives in turn prepared from CO$_2$H derivatives by conventional methods such as homologation.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds,* 6, 324 (1957) Ed. R. C. Elderfield. These 4-carboxy derivatives may be activated by conventional means, e.g. by conversion to an acyl halide or anhydride.

Pyridazines may be prepared by routes analogous to those described in Comprehensive Heterocyclic Chemistry, Volume 3, Ed A. J. Boulton and A. McKillop and napthyridines may be prepared by routes analogous to those described in Comprehensive Heterocyclic Chemistry, Volume 2, Ed A. J. Boulton and A McKillop.

A 4-oxirane derivative of compounds of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

Alternatively and preferably, 4-oxirane derivatives can be prepared from bromomethyl ketones which can be obtained from 4-hydroxy compounds by other routes well known to those skilled in the art. For example, hydroxy compounds can be converted to the corresponding 4-trifluoromethanesulphonates by reaction with trifluoromethanesulphonic anhydride under standard conditions (see K. Ritter, Synthesis, 1993, 735). Conversion into the corresponding butyloxyvinyl ethers can be achieved by a Heck reaction with butyl vinyl ether under palladium catalysis according to the procedure of W. Cabri et al, J. Org. Chem, 1992, 57 (5), 1481. (Alternatively, the same intermediates can be attained by Stille coupling of the trifluoromethanesulphonates or the analaogous chloro derivatives with (1-ethoxyvinyl)tributyl tin, T. R. Kelly, J. Org. Chem., 1996, 61, 4623.) The alkyloxyvinyl ethers are then converted into the corresponding bromomethylketones by treatment with N-bromosuccinimide in aqueous tetrahydrofimran in a similar manner to the procedures of J. F. W. Keana, J. Org. Chem., 1983, 48, 3621 and T. R. Kelly, J. Org. Chem., 1996, 61, 4623.

The 4-hydroxyderivatives can be prepared from an aminoaromatic by reaction with methylpropiolate and subsequent cyclisation, analogous to the method described in N. E. Heindel et al, J. Het. Chem., 1969, 6, 77. For example, 5-amino-2-methoxypyridine can be converted to 4-hydroxy-6-methoxy-[1,5]naphthyridine using this method.

If a chiral reducing agent such as (+) or (−)-B-chlorodiiso-pinocamphenylborane ['DIP-chloride'] is substituted for sodium borohydride, the prochiral chloromethylketone is converted into the chiral chlorohydrin with ee values generally 85-95% [see C. Bolm et al, *Chem. Ber.* 125, 1169-1190, (1992)]. Recrystallisation of the chiral epoxide gives material in the mother liquor with enhanced optical purity (typically ee 95%).

The (R)-epoxide, when reacted with a piperidine derivative gives ethanolamine compounds as single diastereomers with (R)-stereochemistry at the benzylic position.

Alternatively, the epoxide may be prepared from the 4-carboxaldehyde by a Wittig approach using trimethylsulfonium iodide [see G. A. Epling and K-Y Lin, *J. Het. Chem.,* 1987, 24, 853-857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5]naphthyridine-3-carboxylic acid, J. T. Adams et al., *J. Amer. Chem. Soc.,* 1946, 68, 1317). A 4-hydroxy-[1,5]naphthyridine can be converted to the 4-chloro derivative by heating in phosphorus oxychloride, or to the 4-methanesulphonyloxy or 4-trifluoromethanesulphonyloxy derivative by reaction with methanesulphonyl chloride or trifluoromethanesulphonic anhydride, respectively, in the presence of an organic base. A 4-amino 1,5-naphthyridine can be obtained from the 4-chloro derivative by reaction with n-propylamine in pyridine.

Similarly, 6-methoxy-1,5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p 581-627, Ed A. R Katritzky and C. W. Rees, Pergamon Press, Oxford, 1984).

The 4-hydroxy and 4-amino-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1,5-naphthyridines.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 2, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

$R^5CH_2$-halides, acyl derivative $R^5COW$ and $R^5SO_2W$ or aldehydes $R^5CHO$ are commercially available or are prepared conventionally. The aldehydes may be prepared by partial reduction of the $R^5$-ester with lithium aluminium hydride or di-isobutylaluminium hydride or more preferably by reduction to the alcohol, with lithium aluminium hydride or sodium borohydride, followed by oxidation to the aldehyde with manganese (II) dioxide. The aldehydes may also be prepared from carboxylic acids in two stages by conversion to a mixed anhydride for example by reaction with isobutyl chloroformate followed by reduction with sodium borohydride (R. J. Alabaster et al., Synthesis, 598, 1989) to give the hydroxymethyl substituted heteroaromatic or aromatic and then oxidation with a standard oxidising agent such as pyridinium dichromate or manganese (II) dioxide. Acyl derivative $R^5COW$ may be prepared by activation of the $R^5$-acid. $R^5CH_2$-halides such as bromides may be prepared from the alcohol $R^5CH_2OH$ by reaction with phosphorus tribromide in DCM/triethylamine. Alternatively the aldehyde $R^5CHO$ and sulphonic acid derivative $R^5SO_2W$ may be generated by treatment of the $R^5H$ heterocycle with suitable reagents. For example by formylation with hexamine in either trifluoroacetic acid or methanesulfonic acid, in a modified Duff procedure [O. I. Petrov et al. *Collect. Czech. Chem. Commun.* 62, 494-497 (1997)]. Reaction of a $R^5H$ heterocycle with chlorosulphonic acid gives the sulphonic acid derivative (by methods analogous to Techer et. al., *C.R. Hebd. Seances Acad. Sci. Ser. C;* 270, 1601, 1970).

$R^5$ heterocycles are commercially available or may be prepared by conventional methods.

The amines $R^2R^4NH$ are available commercially or prepared conventionally. For example amines $R^5CH_2NH_2$ may be prepared from a bromomethyl derivative by reaction with sodium azide in dimethylformamide (DMF), followed by hydrogenation of the azidomethyl derivative over palladium-carbon. An alternative method is to use potassium phthalimide/DMF to give the phthalimidomethyl derivative, followed by reaction with hydrazine in DCM to liberate the primary amine.

Conversions of $R^{1a'}$, $R^{1'}$, $R^{2'}$, $R^{3'}$ and $R^{4'}$ may be carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial "split and mix" approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLES

Example 1

(R)-2-{4-[(1H-Indol-2-ylmethyl)-amino]-piperidin-1-yl}-1-(6-methoxyquinolin-4-yl)ethanol, dioxalate

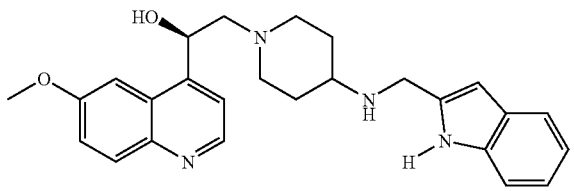

(a) 6-Methoxyquinoline-4-carboxylic acid

The title compound was prepared by modification of the procedure described by W. E. Doering and J. D. Chanley, *J. Amer. Chem. Soc.*, 1946, 68, 586. A mixture of quinone (derived from quinine by reaction with potassium tert-butoxide and benzophenone in toluene) (225 g, 0.70 mol), tert-butanol (1 litre) and water (10 ml) was treated with potassium tert-butoxide (170 g, 1.5 mol). The mixture was stirred at 30° C., while air was bubbled through for 3 days. The mixture was diluted with diethyl ether and water and the layers separated. The aqueous phase was extracted with ethyl acetate. The combined diethyl ether and ethyl acetate extracts were dried over magnesium sulfate and evaporated to give recovered starting material (approximately 100 g). The aqueous phase was acidified to pH5 with 5M hydrochloric acid. The precipitate was collected by filtration, washed with water and methanol, then dried to give 6-methoxyquinoline-4-carboxylic acid as a yellow solid (64.6 g, 46%).

δH (d-6 DMSO) 6.23-5.95 (1H, m), 5.34-5.06 (2H, m), 3.37-2.92 (5H, m), 2.70 (1H, m), 2.38-2.15 (3H, m), 1.94-1.52 (2H, m)

(b) [R]-2-(6-Methoxyquinolin-4-yl)oxirane

A solution of 6-methoxyquinoline-4-carboxylic acid (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyldiazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC). Recrystallisation from ether-pentane gave mother-liquor (7.0 g) (90% ee).

MS (+ve ion electrospray) m/z 202 (MH+)

The absolute stereochemistry was defined to be (R) by an NMR study on the Mosher's esters derived from the product obtained by reaction with 1-t-butylpiperazine.

(c) 4-tert-Butoxycarbonylamino-1-[2-(R)-hydroxy-2-(6-methoxyquinolin-4-yl)]ethylpiperidine To a stirred solution of [R]-2-(6-methoxyquinolin-4-yl) oxirane (Example 1b) (8.07 g, 40.3 mmol) and lithium perchlorate (4.44 g, 40.3 mmol) in anhydrous N,N-dimethylformamide (100 mL) was added 4-tert-butoxycarbonylaminopiperidine hydrochloride (11.0 g, 45.7 mmol) and potassium carbonate (6.72 g, 48.4 mmol). The mixture was heated at 90° C. for 26 h, then cooled, filtered and evaporated. The residue was dissolved in ethyl acetate, washed with water, dried and evaporated. The crude product was chromatographed on silica gel eluted with 2-5% methanol/dichloromethane to give a gum (11.1 g).

MS (+ve ion electrospray) m/z 402 (MH+).

(d) 4-Amino-1-[2-(R)-hydroxy-2-(6-methoxyquinolin-4-yl)]ethylpiperidine

The tert-butoxycarbonylamino compound (1c) (11.11 g, 27.7 mmol) was dissolved in dichloromethane (30 mL), cooled in ice and treated with trifluoroacetic acid (30 mL). The solution was stirred at room temperature for 1.5 h, then evaporated in vacuo. After addition of toluene (50 mL) and re-evaporation, the residue was treated with a 4M solution of hydrogen chloride in 1,4-dioxan (30 mL). The resulting solid was triturated, filtered off and washed with ether. This was then recrystallised by dissolving in hot methanol, concentrating the solution and diluting with dichloromethane, to give the trihydrochloride salt (9.4 g). This was dissolved in water, basified to pH9 and evaporated to dryness. The residue was extracted several times with 10% methanol/dichloromethane (total 600 mL). The extracts were filtered and evaporated to give the free base as a semi-solid foam (6.45 g).

MS (+ve ion Electrospray) m/z 302 (MH+).

(e) Title Compound

A solution of amine (1d) (50 mg, 0.17 mmol) in dichloromethane (1 ml) was treated with 1H indole-2-carboxaldehyde (0.17 mmol) and sodium triacetoxyborohydride (37 mg, 0.18 mmol). After 16 h the reaction mixture was diluted with methanol (1 ml) and sodium borohydride added (70 mg). After 0.5 h the mixture was partitioned between dichloromethane and saturated aqueous sodium bicarbonate solution. The dichloromethane extract was dried and evaporated. The residue was chromatographed on silica eluting with a methanol/dichloromethane gradient affording the title compound as an oil (24 mg, 33%). A solution of this material in deuterochloroform (2 ml) was treated with a solution of oxalic acid (15 mg) in ether (10 ml). The resulting precipitate was centrifuged, then washed by resuspending in ether and centrifuging again. Drying in vacuo afforded the title compound as the dioxalate salt (30 mg).

δH (d6-DMSO-oxalate salt): 1.95 (2H, m), 2.25 (2H, m), 2.95 (2H, m), 3.10-3.30 (3H, m), 3.65 (2H, m), 3.95 (3H, s), 4.40 (2H, s), 5.80 (1H, dd), 7.45 (2H, m), 7.65 (2H, m), 7.80 (1H, t), 7.95-8.10 (1H, t), 8.50 (1H, s), 8.80 (1H, d), 9.05 (1H, s)

MS (+ve ion electrospray) m/z 431 (MH+).

Example 2

(R)-2-{4-[(Quinolin-2-ylmethyl)-amino]-piperidin-1-yl}-1-(6-methoxyquinolin-4-yl)-ethanol, dioxalate

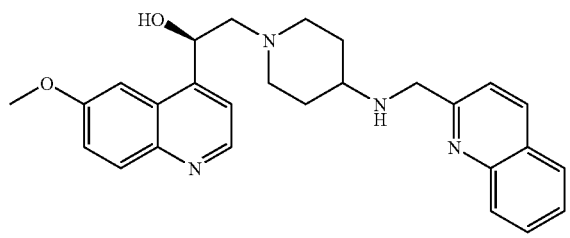

This was prepared from amine (1d) and quinoline-2-carboxaldehyde by the same procedure as Example (1e) affording the title compound as an oil (26 mg, 35%). This was converted to the dioxalate (25 mg) in the same way as for Example 1.

δH (CDCl3-free base): 8.78 (1H, d), 8.10 (3H, m), 7.80 (1H, d), 7.60 (1H, t), 7.55 (1H, d), 7.50 (1H, d), 7.45 (1H, d), 7.35 (1H, dd), 7.15 (1H, d), 5.45 (1H, dd), 4.15 (2H, s), 3.90 (3H, s), 3.30 (1H, m), 2.85 (2H, m), 2.70 (1H, m), 2.45 (2H, m), 2.25 (1H, m), 2.05 (2H, m), 1.60 (2H, m).

MS (+ve ion electrospray) m/z 443 (MH+).

Example 3

(R)-2-{4-[(Benzofuran-2-ylmethyl)-amino]-piperidin-1-yl}-1-(6-methoxyquinolin-4-yl)ethanol, dioxalate

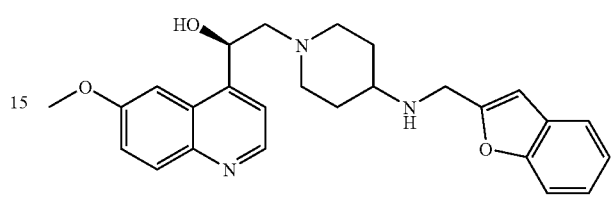

This was prepared from amine (1d) and benzofuran-2-carboxaldehyde by the same procedure as Example (1e) affording the title compound as an oil (25 mg, 34%). This was converted to the dioxalate (32 mg) in the same way as for Example 1.

δH (d6-DMSO-dioxalate salt): 1.95 (2H, m), 2.25 (2H, m), 2.95 (2H, m), 3.10-3.30 (3H, m), 3.65 (2H, m), 3.95 (3H, s), 4.35 (2H, s), 5.80 (1H, dd), 7.05 (1H, s), 7.25-7.40 (2H, m), 7.45-7.50 (2H, m), 7.55-7.70 (3H, m), 7.95 (1H, d), 8.75 (1H,d)

MS (+ve ion electrospray) m/z 432 (MH+).

Example 4

(R)-2-{4-[(Quinolin-3-ylmethyl)-amino]-piperidin-1-yl}-1-(6-methoxyquinolin-4-yl)-ethanol, dioxalate

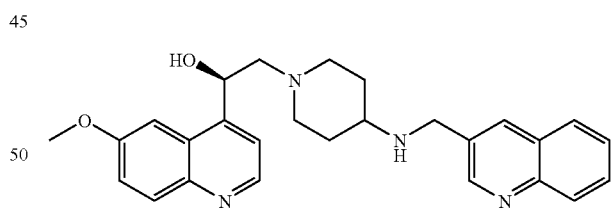

This was prepared from amine (1d) and quinoline-3-carboxaldehyde by the same procedure as Example (1e) affording the title compound as an oil (26 mg, 35%). This was converted to the dioxalate (30 mg) in the same way as for Example 1.

δH (d6-DMSO-dioxalate salt): 1.95 (2H, m), 2.25 (2H, m), 2.95 (2H, m), 3.10-3.30 (3H, m), 3.65 (2H, m), 3.95 (3H, s), 4.40 (2H, s), 5.80 (1H, dd), 7.45 (2H, m), 7.65 (2H, m), 7.80 (1H, t), 7.95-8.10 (3H, m), 8.50 (1H, s), 8.80 (1H, d), 9.05 (1H, s)

MS (+ve ion electrospray) m/z 443 (MH+).

Example 5

(R)-2-{4-[(3-Chloro-benzothiophen-2-ylmethyl)-amino]-piperidin-1-yl}-1-(6-methoxyquinolin-4-yl)-ethanol, dioxalate

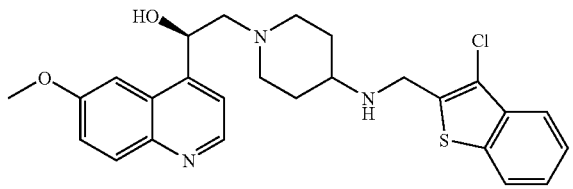

This was prepared from amine (1d) and 3-chlorobenzothiophene-2-carboxaldehyde by the same procedure as Example (1e) affording the title compound as an oil (28 mg, 34%). This was converted to the dioxalate (36 mg) in the same way as for Example 1.

δH (d6-DMSO-dioxalate salt): 1.95 (2H, m), 2.25 (2H, m), 2.95 (2H, m), 3.10-3.30 (3H, m), 3.65 (2H, m), 3.95 (3H, s), 4.35 (2H, s), 5.85 (1H, dd), 7.30 (4H, m), 7.65 (1H, d), 7.80 (1H, d), 8.00 (1H, d), 8.05 (1H, dd), 8.78 (1H, d).

MS (+ve ion electrospray) m/z 482, 484 (MH+).

Example 6

(R)-2-{4-[(Benzofuran-2-ylmethyl)amino]4-hydroxymethyl-piperidin-1-yl}-1-(6-methoxyquinolin-4-yl)-ethanol, dioxalate

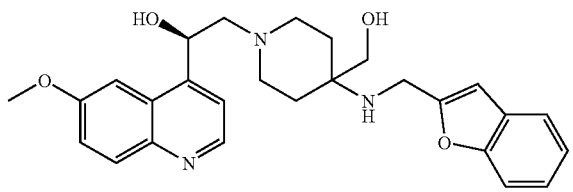

(a) Allyl 4-benzyloxycarbonylaminopiperidine-4-carboxylate

4-Amino-1-tert-butoxycarbonylpiperidine-4-carboxylic acid (18.0 g) was dissolved in 0.03M aqueous sodium hydroxide (750 mL), and 1,2-dimethoxyethane (100 mL). The pH was adjusted to 9.5 with dilute hydrochloric acid, and the suspension was added to an ice-cold solution of N-(benzyloxycarbonyloxy)succinimide (28.8 g) in 1,2-dimethoxyethane (100 mL). The pH was kept at 9.5 by addition of aq. sodium hydroxide, and the mixture was stirred at room temperature. More N-(benzyloxycarbonyloxy)succinimide (3 g) was added after 7 h, then stirring continued overnight. After evaporation to remove the 1,2-dimethoxyethane, the aqueus residue was extracted with ether then acidified to pH4 and extracted with ethyl acetate. This extract was washed with dilute hydrochloric acid, water and brine, dried and evaporated. Trituration of the oily residue gave 4-benzyloxycarbonylamino-1-tert-butoxycarbonylpiperidine-4-carboxylic acid (23 g). This acid (9.62 g) was esterified by treatment with allyl bromide (2.2 mL), potassium carbonate (7.04 g) and potassium iodide (catalytic) in acetone (100 mL) under reflux for 20 h. Evaporation, partitioning of the residue between dichloromethane and water and evaporation of the organic phase gave the allyl ester (10.2 g). This was then treated with trifluoroacetic acid in dichloromethane (1.5 h, room temp.) to give, after basification of the triflate salt and extraction with dichloromethane/methanol, the piperidine free base (6.58 g).

MS (+ve ion electrospray) m/z 319 (MH+)

(b) 4-Benzyloxycarbonylamino-1-[(R)-2-hydroxy-2-(6-methoxyquinolin-4-yl)-ethyl]-piperidine-4-carboxylic acid, allyl ester A solution of piperidine (6a) (1.85 g, 5.8 mmol) and epoxide (1b) (1.2 g, 5.8 mmol) in acetonitrile (10 ml) was treated with lithium perchlorate (0.62 g, 5.8 mmol) and stirred at room temperature for 20 h. The mixture was evaporated and the residue partitioned between dichloromethane and saturated aqueous sodium bicarbonate solution. The dichloromethane extract was dried and evaporated to give an oil. Chromatography on silica eluting with a methanol/dichloromethane gradient afforded the title compound as an oil (1.6 g).

MS (+ve ion electrospray) m/z 520 (MH+).

(c) 4-Amino-1-[(R)-2-hydroxy-2-(6-methoxyquinolin-4-yl)-ethyl]-piperidine-4-carboxylic acid, propyl ester A solution of (6b) (1.58 g) in ethanol (100 ml) was hydrogenated over 10% palladium on charcol (0.1 g) for 16 h. Filtration, evaporation, and chromatography on silica eluting with a methanol/dichloromethane gradient afforded the title compound as an oil (0.53 g).

MS (+ve ion electrospray) m/z 388 (MH+).

(d) (R)-2-(4-Amino-4-hydroxymethylpiperidin-1-yl)-1-(6-methoxyquinolin-4-yl)-ethanol A solution of ester (6c) (0.52 g, 1.3 mmol) in tetrahydrofuran (8 ml) was treated at 0° C. with a solution of lithium aluminium hydride in tetrahydrofuran (1M; 1.4 ml, 1.4 mmol). After 1 h aqueous sodium hydroxide (2M, 20 ml) was added and the mixture was extracted with dichloromethane (30 ml). Drying, evaporation, and chromatography on silica eluting with a methanoydichloromethane gradient afforded the product as an oil (0.24 g).

MS (+ve ion electrospray) m/z 332 (MH+).

(e) Title Compound

A solution of the amine (6d) (50 mg) and benzofuran-2-carboxaldehyde (22 mg) in dichloromethane (2 ml) was treated with sodium triacetoxyborohydride (42 mg). After 0.5 h methanol (1 ml) was added followed by sodium borohydride (20 mg). The mixture was partitioned between dichloromethane and saturated aqueous sodium bicarbonate solution. The dichloromethane extract was dried and evaporated to give an oil. Chromatography on silica eluting with a methanol/dichloromethane gradient afforded the title compound as an oil (55 mg). This was converted to the dioxalate salt (65 mg) by the same procedure as for Example 1.

δH (CDCl3-free base): 2.05 (2H, m), 2.60-2.80 (4H, m), 2.85-3.10 (2H, m), 3.50 (2H, s), 3.85 (2H, 2), 3.95 (3H, s), 5.55 (1H, dd), 6.55 (1H, s), 7.15-7.30 (4H, m), 7.35-7.45 (2H, m), 7.52 (1H, m), 7.65 (1H, d), 8.05 (1H, d), 8.80 (1H, d)

MS (+ve ion electrospray) m/z 462 (MH+).

Example 7

(R)-2-{4-[(1H-Benzimidazol-2-ylmethyl)-amino]-piperidin-1-yl}-1-(6-methoxyquinolin-4-yl)-ethanol, dioxalate

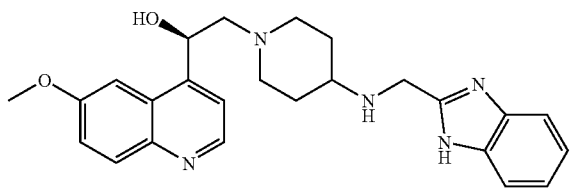

(a) (R)-2-(1,4-Dioxa-8-aza-spiro[4.5]dec-8-yl)-1-(6-methoxyquinolin-4-yl)-ethanol

[R]-2-(6-Methoxyquinolin-4-yl)oxirane (1b) (470 mg) and 1,4-dioxa-8-azaspiro-[4,5]-decane (0.33 ml) were dissolved in dry dichloromethane (5 ml) and ytterbium triflate (30 mol %) was added. The mixture was stirred for 6 hours, filtered through celite, evaporated and chromatographed on silica gel (dichloromethane then methanol-dichloromethane) to afford the title compound (690 mg).

MS (+ve ion electrospray) m/z 345 (MH+).

(b) 1-[(R)-2-Hydroxy-2-(6-methoxy-quinolin-4-yl)-ethyl]-piperidin-4-one

The acetal (7a) was cleaved by treatment with 5M hydrochloric acid (10 ml) in acetone (20 ml) at 60° C. overnight. The mixture was basified with sodium bicarbonate solution and concentrated. Extraction into dichloromethane, evaporation and chromatography on silica gel (dichloromethane then methanol-dichloromethane) gave a yellow gum (482 mg) which solidified on standing. Recrystallisation from boiling ethyl acetate/hexane afforded the product as a pale yellow solid (220 mg), which by chiral hplc was shown to have an enantiomeric excess of >98%.

(c) Title Compound

A mixture of the ketone (7b) (0.1 g), 2-aminomethylbenzimidazole dihydrochloride salt (73 mg), diisopropylethylamine (45 mg), and 3A molecular sieves (0.1 g) in methanol (3 ml) was treated with sodium triacetoxyborohydride (0.18 g) and stirred for 16 h. The mixture was filtered and evaporated. The residue was partitioned between dichloromethane and saturated aqueous sodium bicarbonate solution. The dichloromethane extract was dried and evaporated to give an oil. Chromatography on silica eluting with a methanol/dichloromethane gradient afforded the title compound as an oil (55 mg). This was converted to the dioxalate salt (70 mg) by the same procedure as for Example 1.

δH (CDCl$_3$-free base):1.50 (2H, m), 2.00 (2H, m), 2.1-2.6 (4H, m), 2.80 (2H, m), 3.25 (1H, m), 3.90 (3H, s), 4.20 (2H, s), 5.40 (1H, dd), 7.15 (1H, d), 7.25 (2H, m), 7.35 (1H, dd), 7.60 (3H, m), 8.05 (1H, d), 8.80 (1H,d)

MS (+ve ion electrospray) m/z 432 (MH+).

Example 8

3-({1-[(R)-2-Hydroxy-2-(6-methoxyquinolin-4-yl)-ethyl]-piperidin-4-ylamino}-methyl)-chromen-4-one, dioxalate

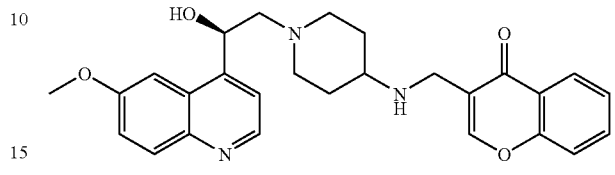

This compound (43 mg) was prepared from amine (1d) 4-oxo-4H-chromene-3-carboxaldehyde by the same procedure as for Example (1e).

MS (+ve ion electrospray) m/z 460 (MH+).

Example 9

(R)-2-{4-[(5-Bromo-1 H-indol-2-ylmethyl)amino]-piperidin-1-yl}-1-(6-methoxy-quinolin-4-yl)-ethanol, dioxalate

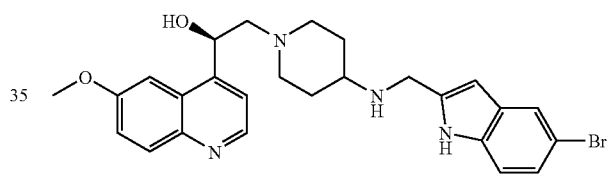

This compound (14 mg) was prepared from amine (1d) and 5-bromo-1H-indole-2-carboxaldehyde by the same procedure as for Example (1e)

MS (+ve ion electrospray) m/z 509 (MH+).

Example 10

(R)-1-(6-Methoxy-quinolin-4-yl)-2-{4-[(6-methyl-1H-benzimidazol-2-ylmethyl)-amino]-piperidin-1-yl}-ethanol, dioxalate

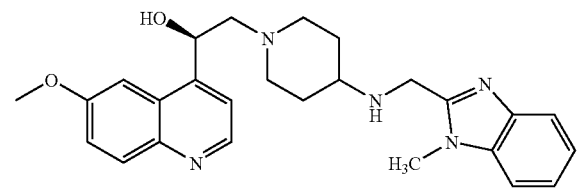

This compound (43 mg) was prepared from amine (1d) and 1-methyl-1H-benzimidazole-2-carboxaldehyde by the same procedure as for Example (1e)

MS (+ve ion electrospray) m/z 446 (MH+).

Example 11

(R)-2-{4-[(6-Methoxy-benzothiazol-2-ylmethyl)-amino]-piperidin-1-yl}-1-(6-methoxy-quinolin-4-yl)-ethanol, dioxalate

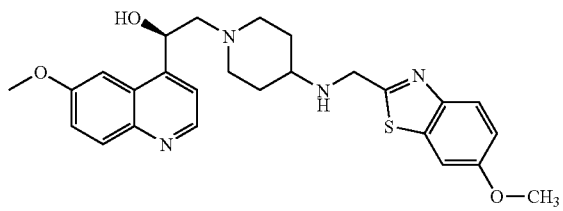

This compound (43 mg) was prepared from amine (1d) and 6-methoxy-benzothiazole-2-carboxaldehyde by the same procedure as for Example (1e).

MS (+ve ion electrospray) m/z 479 (MH+).

Example 12

(R)-2-{4-[(4,6-Difluoro-1H-benzimidazol-2-ylmethyl)-amino]-piperidin-1-yl}-1-(6-methoxyquinolin-4-yl)-ethanol, dioxalate

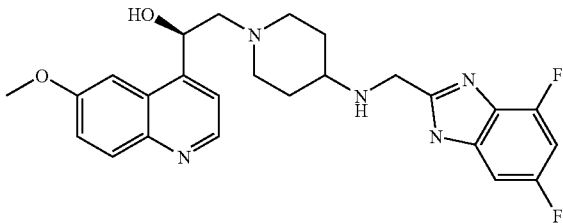

(a) (4,6-Difluoro-1H-benzimidazol-2-yl)-methylamine

A mixture of glycine (2.0 g) and 3,5-difluoro-benzene-1,2-diamine in 5M hydrochloric acid (5 mL) was heated under reflux for 18 hours and evaporated. Sodium carbonate solution was added to pH 10 and the solution was extracted with dichloromethane. The aqueous fraction was evaporated to dryness and the residue was extracted with 5% methanol in chloroform, dried and evaporated to give a foam (0.6 g).

MS (+ve ion electrospray) m/z 184 (MH+).

(b) Title Compound

This was prepared from the amine (12a) (52 mg) and ketone (7b) (0.085 g), by the method of Example (7c) to afforded the title compound as an oil (63 mg).

MS (+ve ion electrospray) m/z 468 (MH+).

$^1$H NMR (CDCl$_3$) δ:1.50 (2H, m), 2.00 (2H, m), 2.1-2.6 (4H, m), 2.80 (2H, m), 3.25 (1H, m), 3.90 (3H, s), 4.20 (2H, s), 5.40 (1H, dd), 6.75 (1H, brt), 7.05 (1H, br d), 7.15 (1H, d), 7.25, 7.35 (1H, dd), 7.60 (1H, d), 8.05 (1H, d), 8.80 (1H,d)

This was converted to the dioxalate salt (78 mg) by the same procedure as for Example 1.

The following compounds (13-15) were prepared by the method of Example 12

Example 13

(R)-2-{4-[(4,5-Difluoro-1H-benzimidazol-2-ylmethyl)-amino]-piperidin-1-yl}-1-(6-methoxyquinolin-4-yl)-ethanol, dioxalate MS (+ve ion electrospray) m/z 468 (MH+)

Example 14

(R)-2-{4-[(5,6-Difluoro-1H-benzimidazol-2-ylmethyl)-amino]-piperidin-1-yl}-1-(6-methoxyquinolin-4-yl)-ethanol, dioxalate MS (+ve ion electrospray) m/z 468 (MH+)

Example 15

(R)-2-{4-[(5-Fluoro-1H-benzimidazol-2-ylmethyl)amino]-piperidin-1-yl}-1-(6-methoxyquinolin-4-y)-ethanol, dioxalate MS (+ve ion electrospray) m/z 450 (MH+)

Example 16

(R)-2-{4-[(4,6-Difluoro-1H-indol-2-ylmethyl)-amino]-piperidin-1-yl}-1-(6-methoxy-quinolin-4-yl)-ethanol, dioxalate

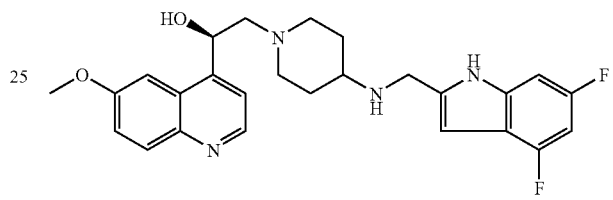

(a) Methyl 2,4-difluoro-α-azidocinnamate

To a solution of 2,4-difluorobenzaldehyde (1.0 g) and ethyl azidoacetate (3.6 g) in methanol (25 ml) at −5 to −10° C. was added a 25% solution of sodium methoxide in methanol (6.0 ml) over 10 min. The mixture was stirred for 2 h at this temperature, then overnight at room temperature. Ether and ammonium chloride (sat. aqueous) were added and the phases were separated. The organic phase was washed with ammonium chloride, dried and evaporated to give the azidoester (1.43 g).

(b) Methyl 4,6-difluoroindole-2-carboxylate

The azidocinnamate (16a) (1.43 g) was heated in toluene under reflux for 3 h. The toluene was evaporated and the residue was chromatographed on silica (1:1 petrol/dichloromethane) to give the indole ester (0.16 g).

MS (+ve ion electrospray) m/z 212 (MH+).

(c) 4,6-Difluoroindole-2-carboxaldehyde

The ester (16b) (0.15 g) in TMF (2 ml) was treated dropwise with lithium aluminium hydride (1M in THF, 0.71 ml) at 0° C. After 1.5 h, additional lithium aluminium hydride (0.1 ml) was added. After 0.5 h the mixture was treated with 8% sodium hydroxide, ethyl acetate and sodium sulphate, filtered and evaporated. The resulting crude alcohol was dissolved in dichloromethane (3 ml) and stirred with manganese (II) oxide for 6 h. Filtration and evaporation of solvent gave the aldehyde (90 mg).

MS (+ve ion electrospray) m/z 182 (MH+).

(d) Title Compound

The aldehyde (16c) (30 mg) and the amine (1d) (50 mg) were stirred in 1:1 dichloromethane/methanol (4 ml) over 3A molecular sieves at room temperature overnight. Sodium borohydride (10 mg) was added and the mixture was stirred for 8 h. The mixture was diluted with dichloromethane, water was added and the phases were separated. The organic phase was washed with water, dried and evaporated.

Chromatography on silica (5-10% methanol/dichloromethane) gave the title compound as the free base (50 mg).

$^1$H NMR (CDCl$_3$)δ: 1.52(m), 1.99(broad t), 2.20(t), 2.38 (t), 2.45-2.65(m), 2.83(dd), 3.28(broad d), 3.92(s), 4.00(s), 5.43(dd), 6.38(s), 6.49(td), 6.87(d), 7.18(d), 7.38(dd), 7.65 (d), 8.04(d), 8.77(d), 8.98(broad).

MS (+ve ion electrospray) m/z 467 (MH+).

A solution of the free base in chloroform was treated with 2 molar equivalents of oxalic acid (0.1 M solution in ether). The resulting precipitate was washed with ether and dried to give the dioxalate salt.

Example 17

(R)-1-(6-Methoxy-quinolin-4-yl)-2-{4-[(1H-pyrrolo [2,3-b]pyridine-2-ylmethyl)-amino]-piperidin-1-yl}-ethanol, dioxalate

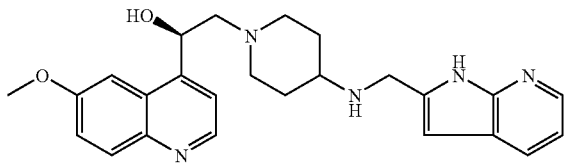

(a) 7-Azaindole-2-carboxylic acid

A solution of 7-azaindole (2.0 g) in THF (30 ml) was cooled to −70° C. and n-butyl lithium (1.6M in hexanes, 11.1 ml) was added dropwise. After 0.5 h at −70° C., carbon dioxide was bubbled through for 10 min, followed by 10 min stirring. The mixture was allowed to warm to 0° C. and the mixture was evaporated under vacuum to approximately half-volume. Fresh THF (15 ml) was added, the mixture was cooled to −70° C. and t-butyl lithium (1.7M in pentane, 10.5 ml) was added dropwise. After stirring for 1 h at −70° C., carbon dioxide was bubbled through for 10 min followed by stirring for 30 min. Water (1.2 ml) was added and the mixture was allowed to warm to room temperature before pouring into saturated ammonium chloride. The aqueous solution was washed with ether, filtered and acidified to pH3.5. The white precipitate was collected and dried to give the acid (2.38 g).

MS (+ve ion electrospray) m/z 163 (MH+).

(b) Methyl 7-azaindole-2-carboxylate

The acid (17a) (1.0 g) was partially dissolved in DMF (20 ml) and methanol (2 ml) and treated dropwise with trimethylsilyldiazomethane (2M in hexanes, 3.1 ml). The mixture was stirred overnight then evaporated. Chromatography on silica (0-20-50-100% ethyl acetate/hexane) gave the ester (0.35 g).

MS (+ve ion electrospray) m/z 177 (MH+).

(c) 7-Azaindole-2-carboxaldehyde

This was prepared (74%) from ester (17b) by the method of Example 16c. MS (+ve ion electrospray) m/z 147 (MH+).

(d) Title Compound

This was prepared from aldehyde (17c) and amine (1d) by the method of Example 16d Chromatography on silica (5% methanol/dichloromethane) gave the free base (35%).

$^1$H NMR (CDCl$_3$) δ: 1.51(m), 1.99(broad t), 2.18(t), 2.38(t), 2.50(m), 2.61(m), 2.80(dd), 3.25(broad d), 3.91(s), 4.07(s), 5.42(dd), 6.30(s), 7.05(dd), 7.16(d), 7.35(dd), 7.63(d), 7.84(d), 8.03(d), 8.28(d), 8.78(d), 10.03(broad).

MS (+ve ion electrospray) m/z 432 (MH+).

The free base was converted into the dioxalate salt by the method of Example 16.

Example 18

R-(1-(6-Methoxy-[1,5]naphthyridin-4-yl)-2-{4-[(quinoxalin-2-ylmethyl)-amino]-piperidin-1-yl}-ethanol, dimethanesulphonate

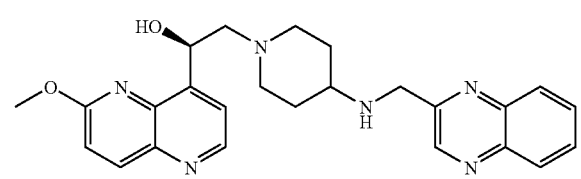

(a) Quinoxaline-2-carboxaldehyde

This was prepared from methyl quinoxaline-2-carboxylate by the method of Example 16c, and used without purification.

This compound can also be prepared by oxidation of 2-methylquinoxaline with selenium dioxide, as described by Landquist et. al J. Chem. Soc. 2052 (1956).

(b) 4-Hydroxy-6-methoxy-[1,5]-naphthyridine

5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystailisation from dichloromethane-hexane (44.6 g, 48%).

The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipitate was filtered to give the title compound (6.26 g, 70%)

(c) Bromomethyl-(6-methoxy-[1,5]-naphthyridin-4-yl)-ketone

The naphthyridine (18b) (10 g, 0.057 mol) in dichloromethane (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified on silica (dichloromethane). The triflate (13.2 g, 0.044 mol) in DMF (200 ml) with triethylamine (12 ml, 0.086 mol) butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in TBF (250 ml), water (40 ml) and treated with N-bromosuccinimide (7.4 g. 0.042 mol) for 1 hour, then evaporated and chromatographed on silica gel (dichloromethane) to give the ketone (10.42 g, 98%).

(d) (R)-2-Bromo-1-(6-methoxy-[1,5]-naphthyridin-4-yl) ethanol

The ketone (18c) (6.6 g, 0.023 mol) in toluene was treated with (+)-B-chlorodiisopinocamphenylborane ((+)-DIP-chlo-

33 ride) (12 g, 0.037 mol) and stirred overnight, then diethanolamine (15 g, 0.14 mol) added and the mixture stirred for 3 hours, filtered and evaporated. Chromatography on silica gel (ethyl acetate-hexane) gave a white solid (4.73 g, 73%).

(e) (R)-2-(6-Methoxy-[1,5]-naphthyridin-4-yl)oxirane

The alcohol (18d) (4.8 g, 0.017 mol) in methanol (20 ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (91% ee by chiral HPLC).

MS (+ve ion electrospray) m/z 203 (MH+).

(f) (R)-1-[2-Hydroxy-2-(6-methoxy-[1,5]naphthyridine-4-yl)]ethyl-4-amino piperidine This was prepared from oxirane (18e) by the Method of Example (1c,d).

(g) Title Compound

This was prepared from the aldehyde (18a) and the amine (18f) by the method of Example 16d. Chromatography on silica (10% methanol/dichloromethane) gave the free base (54%).

$^1$H NMR (CDCl$_3$) δ: 1.61(m), 2.03(broad t), 2.22(t), 2.42 (dd), 2.68(m), 2.86(broad d), 3.09(dd), 3.30(broad d), 4.03(s), 4.23(s), 5.73(dd), 7.11(d), 7.78(m), 8.09(m), 8.20(d), 8.78(d), 8.91(s).

MS (+ve ion electrospray) m/z 445 (MH+).

The free base was dissolved in chloroform and treated with 2 molar equivalents of methanesulphonic acid (0.1M in ether) to give the dimethanesulphonate salt.

Example 19

2({1-[(R)-2-Hydroxy-2-(6-methoxy-quinolin-4-yl)-ethyl]-piperidin-4-ylamino}-methyl)-quinolin-8-ol, dioxalate

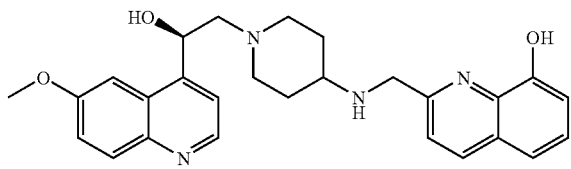

This was prepared from 8-hydroxyquinoline-2-carboxaldehyde and amine (1d) by the method of Example 16d. Chromatography on silica (10-20% methanol/dichloromethane) gave the free base (53%).

$^1$H NMR (CDCl$_3$) δ: 1.62(m), 2.02(broad t), 2.22(t), 2.41 (t), 2.52(dd), 2.69(m), 2.83(dd), 3.28(broad d), 3.92(s), 4.16(s), 5.41(dd), 7.18(m), 7.31(m) 7.39(m), 7.48(d), 7.63 (d), 8.03(d), 8.11(d), 8.77(d)

MS (+ve ion electrospray) m/z 459 (MH+).

The free base was converted into the dioxalate salt by the method of Example 20

34

Example 20

(R)-2-{4-[(Benzo[1,2,3]thiadiazol-5-ylmethyl)-amino]-piperidin-1-yl}-1-(6-methoxy-quinolin-4-yl)-ethanol, dioxalate

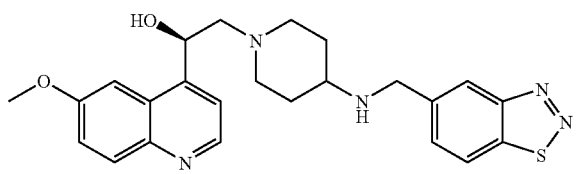

(a) Benzo[1,2,3]thiadiazole-5-carboxaldehyde

This was prepared from methyl benzo[1,2,3]thiadiazole-5-carboxylate (0.291 g) by the method of Example 16c, (except that the alcohol was stirred with manganese (II) oxide overnight) and used without purification.

(b) Title Compound

This was prepared from the aldehyde (20a) and the amine (1d) by the method of Example 16d. Chromatography on silica (10% methanol/dichloromethane) gave the free base as a foam.

$^1$H NMR (CDCl$_3$) δ: 1.60-1.90(m), 2.03(broad t), 2.25(t), 2.38-2.70(m), 2.86(broad d), 3.09(dd), 3.30(broad d), 3.95(s), 4.11(s), 5.47(dd), 7.18(d), 7.38(dd), 7.65(d), 7.75(d), 8.09(m), 8.05(m), 8.60(s), 8.78(d).

MS (+ve ion electrospray) m/z 450 (MH+)

The free base was converted into the dioxalate salt (45 mg) by the method of Example 16.

Example 21

(R)-1-(6-Methoxy-quinolin-4-yl)-2-{4-[(quinoxalin-2-ylmethyl)-amino]-piperidin-1-yl}-ethanol, dioxalate

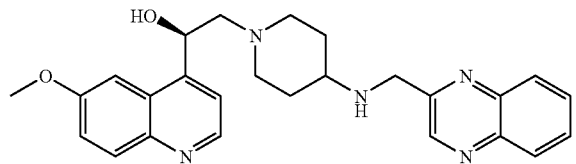

This was prepared from aldehyde (18a) by the method of Example 16d. Chromatography on silica (10% methanol/dichloromethane) gave the free base (38%).

$^1$H NMR (CDCl$_3$) δ: 1.62(m), 2.05(broad t), 2.24(t), 2.43 (t), 2.52(dd), 2.69(m), 2.85(dd), 3.30(broad d), 3.92(s), 4.22(s), 5.43(dd), 7.18(d), 7.37(dd), 7.65(d), 7.78(m), 8.03 (d), 8.10(m), 8.78(d), 8.92(s).

MS (+ve ion electrospray) m/z 444 (MH+).

The free base was converted into the dioxalate salt by the method of Example 16.

Example 22

(R)-1-(6-Methoxy-quinolin-4-yl)-2-{4-[(1-H-pyrrolo[3,2-b]pyridin-2-ylmethyl)-amino]-piperidin-1-yl}-ethanol, dioxalate

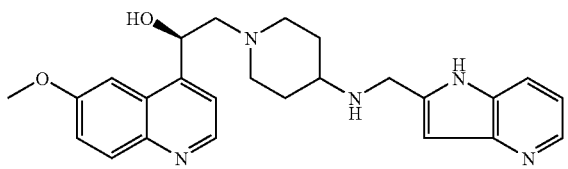

(a) 1H-Pyrrolo[3,2-b]pyridin-2-carboxaldehyde

This was prepared from methyl 1H-pyrrolo[3,2-b]pyridin-2-carboxylate (0.1 g) and amine (1d) by the method of Example 16c, (except that the alcohol was stirred with manganese (II) oxide overnight) and used without purification.

(b) Title Compound

This was prepared from the aldehyde (22a) and the amine (1d) by the method of Example 16d. Chromatography on silica (10% methanol/dichloromethane) gave the free base as a foam.

$^1$H NMR (CDCl$_3$) δ: 1.50(m), 2.00(broad t), 2.19(t), 2.38 (t), 2.42-2.68(m), 2.81(broad d), 3.36(broad d), 3.90(s), 4.09(s), 5.41(dd), 6.04(s), 7.06(m),7.18(d), 7.38(dd), 7.60 (m), 7.60(m), 8.09(m), 8.05(d), 8.41(m), 8.78(d), 9.15(s).

MS (+ve ion electrospray) m/z 432 (MH+)

The free base was converted into the dioxalate salt (69 mg) by the method of Example 16.

Example 23

2-({1-[(R)-2-Hydroxy-2-(6-methoxy-[1,5]naphthyridin-4-yl)-ethyl]-piperidin-4-ylamino}-methyl)-quinolin-8-ol, dimethanesulphonate

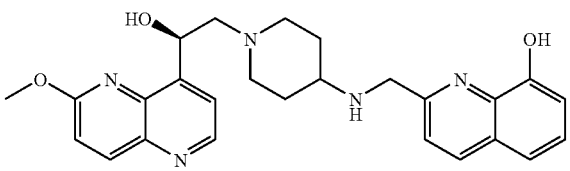

This was prepared from 8-hydroxyquinoline-2-carboxaldehyde and the amine (18f) by the method of Example 16d. Chromatography on silica gel gave the free base.

$^1$H NMR (CDCl$_3$) δ: 1.49-1.73(m), 1.92-2.10(m), 2.1-2.25 (m), 2.31-2.48(m), 2.60-2.74(m), 2.69(m), 2.78-2.81(m), 3.09(dd), 3.25-3.38(m), 4.02(s), 4.16(s), 5.73(dd), 7.05-7.22 (m), 7.26-7.34(m) 7.36-7.48(m), 7.79(d), 8.09(d), 8.20(d), 8.77(d)

MS (+ve ion electrospray) m/z 460 (MH+).

The free base was converted into the dimethanesulphonate salt as for Example 18.

Example 24

(R)-2-{4-[(4-Fluoro-1H-benzimidazol-2-ylmethyl)-amino]-piperidin-1-yl}-1-(6-methoxyquinolin-4-yl)-ethanol, dioxalate

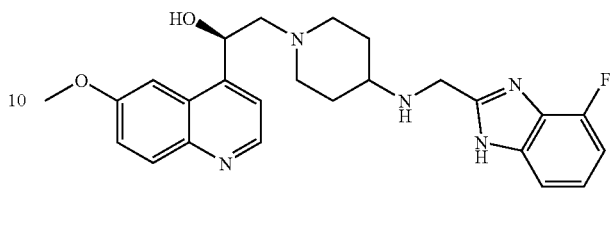

(a) 3-Fluoro-benzene-1,2-diamine

A solution of 2-fluoro-6-nitro-phenylamine [K. L. Kirk and L. A. Cohen *J. Org. Chem.* 34, 384-389 (1969)] (1.05 g) in ethanol (50 ml) was hydrogenated over 10% palladium on carbon (0.5 g), filtered and evaporated to give a brown solid, used without purification.

MS (+ve ion electrospray) m/z 127 (MH+).

(b) (4-Fluoro-1H-benzimidazol-2-yl)-methylamine

A mixture of glycine (7.0 g) and 3-fluoro-benzene-1,2-diamine (28a) in 5M hydrochloric acid (5 mL) was heated under reflux for 20 hours and evaporated. Sodium carbonate solution was added to pH 10 and the solution was extracted with dichloromethane. The aqueous fraction was evaporated to dryness and the residue was extracted with 10% methanol in chloroform, dried and evaporated to give a foam (0.53 g).

MS (+ve ion electrospray) m/z 166 (MH+).

(c) Title Compound

This was prepared from the amine (24b) (93.5 mg) and recrystallised ketone (7b) (0.17 g), by the method of Example (7c). Purification on silica gel (2-15% methanol-dichloromethane) afforded the title compound as an oil (0.102 g).

MS (+ve ion electrospray) m/z 450 (MH+).

$^1$H NMR (CDCl$_3$) δ:1.50 (2H, m), 2.00 (2H, broad t), 2.10-2.60 (4H, m), 2.80 (2H, broad dd), 3.25 (1H, broad d), 3.90 (3H, s), 4.20 (2H, s), 5.41 (1H, dd), 6.95 (1H, m), 7.15 (2H, m), 7.35 (2H, m), 7.62 (1H, d), 8.05 (1H, d), 8.80 (1H,d)

This was converted to the dioxalate salt (0.13 g) by the method of Example 16.

Example 25

(R)-2-{4-[(Benzothiazol-2-ylmethyl)-amino]-piperidin-1-yl}-1-(6-methoxy-quinolin-4-yl)-ethanol, dioxalate

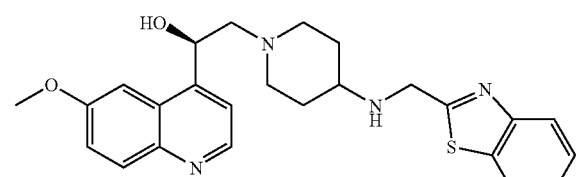

(a) 2-Chloromethyl-benzothiazole

This was prepared from 2-amino-benzenethiol by the method of B. C. Mylari et al [Syn. Commun. 19, 29214 (1989)]

(b) Title Compound

A solution of the amine (1d) 0.2 g) and 2-chloromethyl-benzothiazole (25a) (0.122 g) in dry DMF (3 ml) containing diisopropylethylamine (0.2 ml) and potassium iodide (4 crystals) was stirred at room temperature for 18 h and evaporated to dryness. Sodium bicarbonate solution was added and the mixture was extracted with dichloromethane, washed with water and dried over sodium sulfate. The product was chromatographed on silica gel (2-5% methanol-dichloromethane) to afford a foam (0.066 g).

MS (+ve ion electrospray) m/z 449 (MH+).

$^1$H NMR (CDCl$_3$) δ:1.55 (2H, m), 2.05 (2H, broad t), 2.15-2.75 (4H, m), 2.85 (2H, broad dd), 3.30 (1H, broad d), 3.91 (3H, s), 4.29 (2H, s), 5.48 (1H, dd), 7.19 (1H, d), 7.40 (3H, m), 7.65 (1H, d), 7.90 (1H, d), 8.00 (1H, d), 8.04 (1H, d), 8.78 (1H, d)

This was converted to the dioxalate salt (0.09 g) by the method of Example 16.

Example 26

(R)-2-(4-{[(R)-1-(2,3-Dihydro-[1,4]dioxino[2,3-]pyridin-3-yl)methyl]-amino}-piperidin-1-yl)-1-(8-fluoro-6-methoxy-quinolin-4-yl)-ethanol, dioxalate

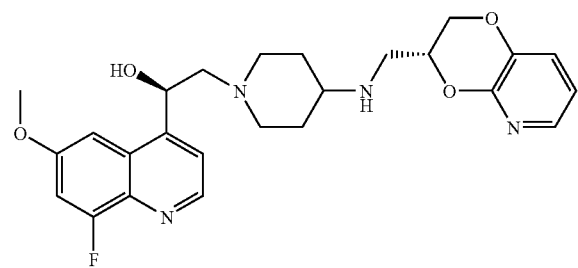

(a) 8-Fluoro-6-methoxy-quinolin-4-ol

2-Fluoro-4-methoxy-phenylamine (3.80 g, 26.7 mmol) and methyl propiolate (2.37 ml, 0.267 mol) in methanol (10 ml) was stirred for 72 hours at room temperature, then heated at 50° C. for 24 hours. It was evaporated and the product purified by chromatography on silica gel (dichloromethane) to give a solid (1.66 g), a portion of which was recrystallised from dichloromethane-hexane.

The unsaturated ester (0.96 g) in warm Dowtherm A (5 ml) was added over 3 minutes to refluxing Dowtherm A (15 ml), and after a further 20 minutes at reflux the mixture was cooled and poured into ether. The precipitate was filtered to give the title compound (0.50 g, 61%).

(b) 1,1,1-Trifluoro-methanesulfonic acid 8-fluoro-6-methoxy-quinolin-4-yl ester

The quinolinol (26a) (0.48 g) and dimethylaminopyridine (0.03 g) in dichloromethane (20 ml) and 2,6-lutidine (0.48 ml) was treated dropwise with triflic anhydride (0.48 ml) and the mixture was stirred at room temperature for 4 hours. It was washed with saturated ammonium chloride, dried, evaporated, and chromatographed on silica gel (dichloromethane) to afford a yellow solid (0.69 g).

MS (+ve ion electrospray) m/z 326 (MH+).

(c) 2-Bromo-1-(8-fluoro-6-methoxy-quinolin-4-yl)-ethanone

The triflate (26b) (19.1 g) was converted to the bromomethyl ketone (8.6 g) by the method of Example (18c).

MS (+ve ion electrospray) m/z 298/300 (MH+).

(d) 8-Fluoro-6-methoxy-4-(R)-oxiranyl-quinoline

The bromomethyl ketone (26c) (8.6 g) was converted to the oxirane (1.04 g) by the methods of Examples (18d,e).

MS (+ve ion electrospray) m/z 220 (MH+).

(e) 1-[(R)-2-(8-Fluoro-6-methoxy-quinolin-4-yl)-2-hydroxy-ethyl]-piperidin-4-one This was prepared from oxirane (26d) (1.04 g) by the Method of Example (7a,b) to give the ketone (1.1 g), as a foam.

MS (+ve ion electrospray) m/z 319 (MH+).

(e) Title Compound

This was prepared from ketone (26e) (0.10 g) and C—[(R)-1-(2,3-Dihydro-[1,4]dioxino[2,3-b]pyridin-3-yl)]-methylamine [C. Comoy et al. Med. Chem. Res. 6, 392-399 (1996)]) (0.055 g) by the method of Example (7c). Purification on silica gel (2-10% methanol-dichloromethane) afforded the title compound as a foam (0.093 g).

MS (+ve ion electrospray) m/z 469 (MH+).

$^1$H NMR (CDCl$_3$) δ: 1.50 (2H, m), 1.95 (2H, broad t), 2.20-2.60 (4H, m), 2.80 (2H, broad dd), 2.95 (2H, m), 3.25 (1H, broad d), 3.90 (3H, s), 4.10 (1H, m), 4.28 (1H, dd), 4.45 (1H, m), 5.40 (1H, dd), 6.88 (1H, m), 7.00 (1H, s), 7.12 (1H, dd), 7.25 (1H, dd), 7.70 (1H, d), 7.82 (1H, m), 8.80 (1H,d)

This was converted to the dioxalate salt (0.131 g) by the method of Example 16.

Example 27

1-{4[(8-Hydroxy-quinolin-2-ylmethyl)-amino]-piperidin-1-yl}-2-(6-methoxy-quinolin-4-yl)-ethanone, oxalate

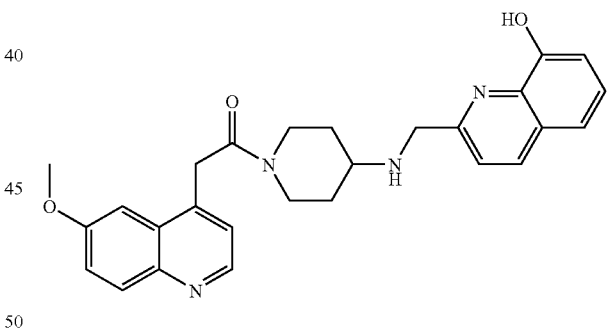

(a) (6-Methoxy-quinolin-4-yl)-acetic acid ethyl ester

6-Methoxy-4-methyl-quinoline (0.791 g, 4.572 mmol) was dissolved in anhydrous diethyl ether and cooled to 0° C. under an argon atmosphere. To the stirred mixture was added sodamide as a 50% w/w slurry in toluene (0.36 g, 4.57 mmol). The resulting slurry was allowed to warm to room temperature and was stirred for 1 hour. To this was added diethylcarbonate (0.28 ml, 2.29 mmol). The reaction mixture was then stirred at reflux for 10 hours after which time it was quenched with water (2 ml). The mixture was partitioned between ethyl acetate (2×100 ml) and water (20 ml). The organic phases were combined and dried over magnesium sulfate. The volatiles were removed under reduced pressure and the residue subjected to purification on silica gel using an ethyl acetate-hexane gradient. This provided the desired product as a brown oil (90 mg, 7%).

MS (APCI+) m/z 246 (MH+).

(b) {1 [2-(6-Methoxy-quinolin-4-yl)-ethanoyl]-piperidin-4-yl}-carbamic acid tert-butyl ester The ester (27a) (90 mg, 0.367 mmol) was dissolved in a mixture of tetrahydrofuran and water (3:1, 3 ml) and sodium hydroxide (44 mg, 1.10 mmol) was added. The solution was stirred at room temperature for 10 hours and then the solvent was removed under reduced pressure. The residue was re-dissolved in aqueous hydrochloric acid (1N, 5 ml) and then the solvent removed in vacuo. The residue obtained was dissolved in N,N'-dimethylformamide (3 ml) and to this was added O-(7-azabenzotriazol-1-yl)-N,N,N'N'-tetramethyluronium hexafluorophosphate (139 mg, 0.367 mmol), piperidin-4-yl-carbamic acid tert-butyl ester (80 mg, 0.404 mmol) and diisopropylethylamine (0.19 ml, 1.10 mmol). The resulting solution was stirred at room temperature for 10 hours. The solvent was then removed under vacuum and the residue partitioned between ethyl acetate (2×100 ml) and water (20 ml). The organic phases were combined and dried over magnesium sulfate then concentrated under reduced pressure. The resultant oil was purified on silica gel using an ethyl acetate-hexane gradient. This provided the desired compound as a white solid (139 mg, 95%).

MS (APCI+) m/z 400 (MH+).

(c) Title Compound

The amide (27b) (177 mg, 0.444 mmol) was dissolved in dichloromethane (2 ml) and trifluoroacetic acid (1 ml) was added. The resulting solution was stirred at room temperature for 2 hours after which time the volatiles were removed under reduced pressure. The residue was dissolved in dichloromethane and methanol (3:1, 3 ml) and 4 Ø molecular sieves were added (1 g). To the solution 8-hydroxy-quinoline-2-carboxaldehyde (77 mg, 0.444 mmol) was added and allowed to stir at room temperature under argon for 10 hours. Sodium borohydride (34 mg, 0.888 mmol) was then added to the reaction mixture and stirred for a further 3 hours at room temperature. The mixture was quenched by the addition of water (2 ml). The volatiles were removed in vacuo and the residue partitioned between ethyl acetate (2×100 ml) and water (20 ml). The organic phases were combined and dried over magnesium sulfate. The solvent was removed under reduced pressure and the residue purified on silica gel using a dichloromethane-methanol gradient. This provided the desired compound as a colourless oil (17 mg, 8%).

$^1$H NMR (CDCl$_3$) δ: 1.40-1.60 (4H, m), 1.85-2.00 (2H, m), 2.75-3.00 (2H, m), 3.16 (1H, m), 3.81 (1H, m), 3.97 (3H, s), 4.13 (2H, s), 4.17 (2H, s), 4.45 (1H, m), 7.19 (1H, dd), 7.30 (2H, m), 7.34 (1H, d), 7.52 (2H, m), 7.56 (1H, dd), 8.13 (1H, d), 8.91-8.95 (2H, m).

MS (APCI+) m/z 457 (MH+).

The oxalate salt was generated in a manner similar to Example 1.

Example 100

(R)-2-{4-[(Benzothiazol-5-ylmethyl)-amino]-piperidin-1-yl}-1-(6-methoxyquinolin-4-yl)-ethanol, dioxalate

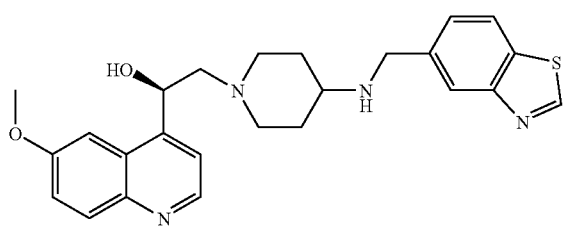

(a) Benzothiazole-5-carboxylic acid

4-Chloro-3-nitro-benzoic acid (22 g) was suspended in water (750 ml) containing sodium hydroxide (4.33 g) and sodium sulfide hydrate (32 g) was added and the mixture was heated under reflux for 24 hours. It was neufralised with 5M hydrochloric acid and extracted with ethyl acetate to afford a foam (13.5 g), which was heated under reflux in formic acid (300 ml) containing zinc dust (1.5 g) for 6 hours. The reaction mixture was cooled, filtered and evaporated and the residue was diluted with water, adjusted to pH 6.5 and evaporated to dryness. It was chromatographed on silica get (methanol-dichloromethane then methanol-ethyl acetate) to give the product (10.4 g).

MS (–ve ion electrospray) m/z 178 (M–H)$^-$.

(b) Benzothiazol-5-yl-methanol

The acid (100a) (0.53 g) in tetrahydrofuran (20 ml) and triethylamine (0.49 ml) was cooled to 0° C. and isobutylchloroformate (0.42 ml) was added dropwise and the solution was stirred at 0° C. for 1 hour, when it was filtered into a stirred solution of sodium borohydride (0.24 g) in ice/water (50 ml). The mixture was stirred at 0° C. for 0.5 hour, neutralised with 2M hydrochloric acid, evaporated to half volume, and extracted with dichloromethane. The organic fraction was dried, evaporated to dryness and chromatographed on silica gel (ethyl acetate) to give the alcohol (0.345 g)

MS (+ve ion electrospray) m/z 166 (MH)$^+$ (c) Benzothiazole-5-carboxaldehyde

A stirred solution of the alcohol (100b) (0.61 g) in dichloromethane (25 ml) was treated with manganese dioxide (3.6 g) for 18 hours and was filtered and evaporated to give a solid (0.505 g).

MS (+ve ion electrospray) m/z 164 (MH)$^+$ (d) Title Compound

A solution of theamine (1d; 94% ee) (0.70 g) and carboxaldehyde (100c) (0.505 g) in dichloromethane (15 ml) and methanol (15 ml) was treated with 3A molecular sieves and the mixture was stirred at room temperature for 18 hours. The mixture was treated with sodium borohydride (140 mg) in portions and after 18 hours the solution was diluted with water, extracted with dichloromethane and chromatographed on silica gel (methanol-dichloromethane) to afford the free base of the title compound as an oil (0.559 g).

δH (CDCl$_3$): 1.50-2.10 (6H, m), 2.20-2.70 (2H, m), 2.85 (2H, m), 3.30 (1H, m), 3.90 (3H, s), 4.05 (2H, s), 5.45 (1H, dd), 7.20 (1H, d) 7.35 (1H, dd), 7.48 (1H, d), 7.62 (1H, d), 7.90 (1H, d), 8.05 (1H, d), 8.10 (1H, s), 8.75 (1H, d), 9.0 (1H, s).

MS (+ve ion electrospray) m/z 449 (MH$^+$).

The dioxalate salt was prepared by the same method as for Example 1.

The following Examples were prepared by analogous methods.

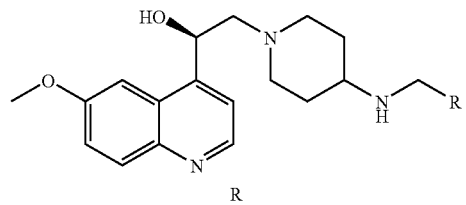

| Example | Method of synthesis | salt AY dioxalate DZ dimesylate R trihydrochloride | R |
|---|---|---|---|
| 50 | A | AY | 4,7-difluoro-1H-indol-2-yl |
| 51 | A | AY | 7-nitro-1H-indol-2-yl |
| 52 | A | AY | 4-fluoro-1H-indol-2-yl |
| 53 | A | AY | 1H-pyrrolo[2,3-b]pyridin-2-yl |
| 54 | A | AY | 4-chloro-1H-indol-2-yl |
| 55 | A | AY | 2-chloro-quinolin-3-yl |
| 56 | A | AY | 3-methyl-benzofuran-2-yl |
| 57 | A | AY | 5-fluoro-1H-indol-2-yl |
| 58 | A | AY | isoquinolin-3-yl |
| 59 | B | AY | 2,3-dihydrobenzo[1,4]dioxin-2-yl |
| 60 | A | AY | benzo[b]thiophen-2-yl |
| 61 | A | AY | 5-methylbenzothiophen-2-yl |
| 62 | A | AY | 5,7-difluoro-1H-indol-2-yl |
| 63 | C | AY | benzoxazol-2-yl |
| 64 | A | AY | 6-chloro-1H-indol-2-yl |
| 65 | C | DZ | 7-fluoro-3-methyl-3H-quinazolin-4-one-2-yl |
| 66 | A | AY | 6-cyano-1H-indol-2-yl |
| 67 | C | AY | 4,5-difluorobenzoxazol-2-yl |
| 68 | A | AY | 5-nitro-1H-indol-2-yl |
| 69 | C | DZ | imidazo[1,2-a]pyridin-2-yl |
| 70 | A | AY | 3,6-dichloro-1H-indol-2-yl |
| 71 | A | AY | 1H-indol-6-yl |
| 72 | A | AY | 5-chloro-1H-indol-2-yl |
| 73 | C | AY | 3H-quinazolin-4-one-2-yl |
| 74 | C | DZ | 6,7-difluoro-3H-quinazolin-4-one-2-yl |
| 75 | A | AY | 7-methoxybenzofuran-2-yl |
| 76 | C | AY | 5-fluoro-benzoxazol-2-yl |
| 77 | A | AY | 5-methoxy-benzofuran-2-yl |
| 78 | C | DZ | 5-fluoro-3H-quinazolin-4-one-2-yl |
| 79 | A | DZ | benzo[1,2,5]-oxadiazol-5-yl |
| 80 | A | AY | 5-trifluoromethoxy-1H-indol-2-yl |
| 81 | C | AY | 6-fluoro-benzoxazol-2-yl |
| 82 | C | AY | oxazolo[4,5-b]-pyridin-2-yl |
| 83 | B | DZ | 3H-imidazo[4,5-b]-pyridin-2-yl |
| 84 | C | AY | 6-fluoro-imidazo[1,2-a]pyridin-2-yl |
| 85 | a | R | 2-hydroxyquinolin-3-yl |
| 86 | A | AY | 4-benzyloxy-1H-indol-2-yl |
| 87 | b | DZ | 4-hydroxy-1H-indol-2-yl |
| 88 | A | AY | 7-methanesulphonyl-1H-indol-2-yl |
| 89 | C | AY | imidazo-[1,2-a]-pyrimidin-2-yl |
| 90 | A | AY | 2-methyl[1,8]-naphthyridine-3-yl |
| 91 | A | AY | 5-benzyloxy-1H-indol-2-yl |
| 92 | A | AY | 3-fluoro-1H-indol-2-yl |
| 93 | A | AY | benzo[1,2,5]thiadiazol-5-yl |
| 94 | B | DZ | 3-(R)-(2,3-Dihydro-[1,4]dioxino[2,3-b]pyridin-3-yl |
| 95 | A | AY | 8-hydroxyquinoxalin-2-yl |
| 96 | A | AY | cinnolin-3-yl |
| 97 | A | AY | 6-chloro-1H-pyrrolo[2,3-b]pyridin-2-yl |
| 98 | A | AY | 5-hydroxyquinoxalin-2-yl |
| 99 | A | AY | pyrazolo[1,5-a]pyridin-2-yl |
| 101 | A | AY | 3-fluoropyrazolo[1,5-a]pyridin-2-yl |
| 102 | A | R | 8-hydroxy-2H-isoquinolin-1-one-3-yl |
| 103 | C | DZ | pyrido[1,2-a]pyrimidin-4-one-2-yl |
| 104 | A | AY | 6-fluoropyrazolo[1,5-a]pyridin-2-yl |
| 105 | B | AY | 4-nitro-1H-benzimidazol-2-yl |
| 106 | B | AY | 4-fluoro-1H-benzimidazol-2-yl |
| 107 | A | AY | 5-trifluoromethyl-thieno[3,2-b]pyridin-6-yl |
| 108 | C | DZ | 7-fluoro-3-methyl-3H-quinazolin-4-one-2-yl |
| 109 | A | AY | imidazo[1,2-b]pyridazin-2-yl |
| 110 | C | AY | quinazolin-2-yl |
| 111 | A | AY | quinoxalin-6-yl |
| 112 | C | AY | 7-fluoro-quinazolin-2-yl |
| 113 | B | AY | 3-(R,S)-3,4-dihydro-2H-benzo[1,4]thiazin-3-yl |
| 114 | A | AY | 7-benzyloxy-1H-indol-2-yl |
| 115 | A | AY | benzo[1,2,3]thiadiazol-6-yl |
| 116 | C | DZ | thiazolo[3,2-a]pyrimidin-5-one-7-yl |
| 117 | B | AY | thiazolo[5,4-b]pyridin-2-yl |
| 118 | A | AY | pyrido[1,2-a]pyrimidin-4-one-3-yl |

-continued

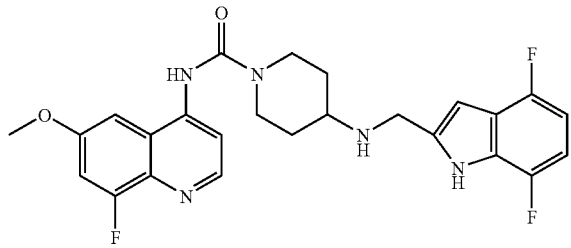

| Example | Method of synthesis | salt<br>AY dioxalate<br>DZ dimesylate<br>R trihydrochloride | R |
|---|---|---|---|
| 119 | A | AY | 1-isopropyl-1H-benzotriazol-5-yl |
| 120 | B | AY | 4-cyano-1H-benzimidazol-2-yl |
| 121 | C | AY | 6-chloro-imidazo[1,2-b]pyridazine-2-yl |
| 122 | A | AY | 3H-benzothiazol-2-one-5-yl |
| 123 | B | DZ | 3-(S)-(2,3-dihydro-[1,4]dioxino[2,3-b]pyridin-3-yl |
| 124 | A | AY | 5-chloro-3H-benzooxazol-2-one-6-yl |

<sup>a</sup> Prepared from Example 55 by heating in 5 M HCl/dioxan (1:1) under reflux for 18 hours
<sup>b</sup> Prepared from Example 86 by hydrogenation over palladium/carbon
A: by method of Example 16
B: by method of Example 7
C: by method of Example 25

Example 150

4-[(4,7-Difluoro-1-H-indol-2-ylmethyl)-amino]-piperidine-1-carboxylic acid (8-fluoro-6-methoxy-quinolin-4-yl)-amide, oxalate (a) 8-Fluoro-6-methoxy-quinolin-4-ylamine A solution of the triflate (26b) (0.69 g) in pyridine (10 ml) was treated with n-propylamine hydrochloride (1.2 g) and the mixture heated at reflux for 16 hours. The reaction mixture was evaporated, disolved in 0.05M HCl, washed with dichloromethane, basified with sodium hydroxide solution and re-extracted with dichloromethane. The combined organics were dried ($Na_2SO_4$), evaporated, and chromatographed on silica gel (2-5% methanol in dichloromethane) to afford an orange solid (1.0 g).

MS (+ve ion electrospray) m/z: 193 (MH$^+$).

(b) 4-(1-Imidazolylcarbonyl)amino-8-fluoro-6-methoxyquinoline

A suspension of the amine (150a) (0.213 g) in ethanol-free chloroform (5 ml) was treated with 4-N,N-dimethylaminopyridine (0.153 g) and 1,1'-carbonyl diimidazole (0.246 g) for 5.5 hours and the reaction mixture was filtered, evaporated to dryness, and used without purification.

(c) [1-(8-Fluoro-6-methoxy-quinolin-4-ylcarbamoyl)-piperidin-4-yl]-carbamic acid tert-butyl ester To a stirred solution of the imidazolylcarbonyl compound (150b) in anhydrous DMF (3 ml) was added 4-tert-butoxycarbonylaminopiperidine hydrochloride (0.26 g) and potassium carbonate (0.15 g). The mixture was heated at 70° C. for 12 hours, then cooled, filtered and evaporated. The residue was dissolved in ethyl acetate, washed with water, dried and evaporated. The crude product was chromatographed on silica gel eluted with 2-4% methanol/dichloromethane to give a gum (0.465 g).

MS (+ve ion electrospray) m/z 419 (MH+)

(d) 4-Amino-piperidine-1-carboxylic acid (8-fluoro-6-methoxy-quinolin-4-yl)-amide The tert-butoxycarbonylamino compound (150c) (0.465 g) was dissolved in dichloromethane (4 ml), cooled in ice, and treated with trifluoroacetic acid (3 ml). The solution was stirred at room temperature for 2 hours, then evaporated in vacuo. The residue was basified with sodium bicarbonate solution and evaporated. It was extracted with 10% methanol/dichloromethane, dried and evaporated to give a foam.

MS (+ve ion electrospray) m/z 317 (MH+)

(e) Ethyl 4,7-difluoroindole-2-carboxylate

A mixture of 2,5-difluorophenylhydrazine (4.0 g), ethyl pyruvate (3.1 ml) and glacial acetic acid (40 ml) was heated under reflux for 1.5 h. The mixture was evaporated, then toluene was added and re-evaporated. The crude product (6.7 g) was heated under reflux with anhydrous p-toluenesulphonic acid (19.1 g) for 5.5 h.

The cooled mixture was dissolved in ethyl acetate, washed with sodium bicarbonate and brine, dried and evaporated. Chromatography on silica gel (1:1 dichloromethane/petrol) followed by recrystallization (dichloromethane/hexane) gave the indole ester (0.75 g).

(f) 4,7-Difluoroindole-2-carboxaldehyde

This was prepared (55%) from the ester (150e) by the method of Example (16c).

MS (+ve ion electrospray) m/z 182 (MH+).

(g) Title Compound

A mixture of amine (150d) (0.10 g) and 4,7-difluoro-1H-indole-2-carboxaldehyde (150f) (0.06 g) and 3A molecular sieves in dichloromethane (4 ml) and methanol (4 ml) was stirred at room temperature for 6 hours, sodium borohydride was added and the mixture was stirred for a further 24 hours. It was quenched with water and the organic layer separated, dried, evaporated and chromatographed on silica gel (2% methanol/dichloromethane) to afford a solid (0.042 g).

MS (+ve ion electrospray) m/z 484 (MH+)

This was converted to the oxalate salt by the method of Example 16.

The Examples 151 and 152 were prepared by analogous methods to Example 150

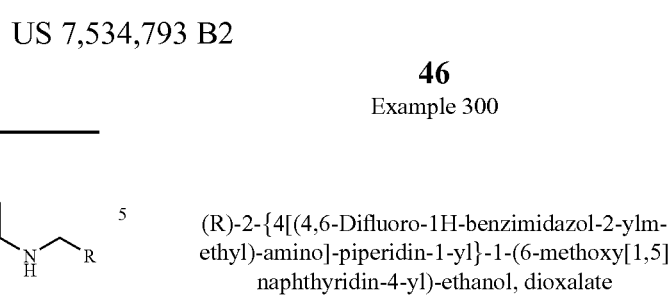

| Example | salt G oxalate | R |
|---|---|---|
| 151 | G | 8-hydroxyquinoxalin-2-yl |
| 152 | G | 8-hydroxyquinolin-2-yl |

The Examples 170 and 171 were prepared by analogous methods to Example 26

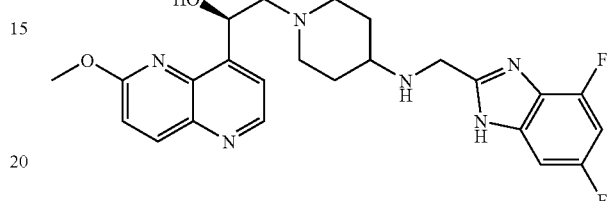

| Example | salt AY di-oxalate | R |
|---|---|---|
| 170 | AY | 4-fluoro-1H-benzimidazol-2-yl |
| 171 | AY | 3H-imidazo[4,5-b]pyridin-2-yl |

Examples 180 and 181 were prepared from 6-trifluoromethoxy-quinolin-4-ylamine by the method of Example 150

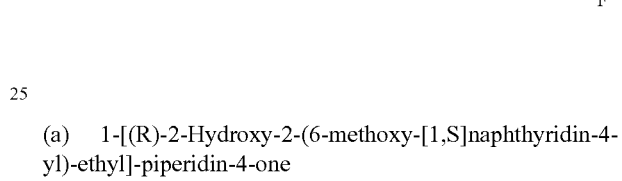

| Example | salt G oxalate | R |
|---|---|---|
| 180 | G | 8-hydroxyquinoxalin-2-yl |
| 181 | G | 5-hydroxyquinoxalin-2-yl |

Example 300

(R)-2-{4[(4,6-Difluoro-1H-benzimidazol-2-ylm-ethyl)-amino]-piperidin-1-yl}-1-(6-methoxy[1,5]naphthyridin-4-yl)-ethanol, dioxalate (a)  1-[(R)-2-Hydroxy-2-(6-methoxy-[1,S]naphthyridin-4-yl)-ethyl]-piperidin-4-one This was prepared from the oxirane (18e) by the method of Example (7a and b), and had an enantiomeric excess of 90%.

MS (+ve ion electrospray) m/z 302 (MH+)

Title Compound

This was prepared from ketone (300a) and amine (12a) by the method of Example (7c)

MS (+ve ion electrospray) m/z 469 (MH+)

This was converted to the oxalate salt by the method of Example 16

The following Examples were prepared by analogous methods.

| Example | Method of synthesis | salt AY dioxalate DZ dimesylate | R |
|---|---|---|---|
| 301 | D | DZ | 4,7-difluoro-1H-indol-2-yl |
| 302 | D | AY | 1H-indol-2-yl |
| 303 | D | DZ | 4,6-difluoro-1H-indol-2-yl |
| 304 | D | AY | isoquinolin-3-yl |
| 305 | E | AY | benzoxazol-2-yl |
| 306 | D | AY | 1H-pyrrolo[2,3-b]pyridin-2-yl |
| 307 | E | AY | imidazo[1,2-a]pyridin-2-yl |

-continued

| Example | Method of synthesis | salt AY dioxalate DZ dimesylate | R |
|---|---|---|---|
| 308 | E | AY | 4-fluoro-1H-benzimidazol-2-yl |
| 309 | E | DZ | 3-(R)-(2,3-Dihydro-[1,4]dioxino[2,3-b]pyridin-3-yl |
| 310 | E | DZ | 3-(S)-(2,3-Dihydro-[1,4]dioxino[2,3-b]pyridin-3-yl |
| 311 | D | AY | benzo[1,2,3]thiadiazol-5-yl |
| 312 | D | AY | imidazo[1,2-a]pyridazin-2-yl |
| 313 | D | AY | 3-fluoropyrazolo[1,5-a]pyridin-2-yl |

D: by method of Example 18
E: by method of Example 300

Example 400

4-[(4,7-Difluoro-1H-indol-2-ylmethyl)-amino]-piperidine-1-carboxylic acid (6-methoxy-[1,5]naphthyridin-4-yl)-amide, oxalate

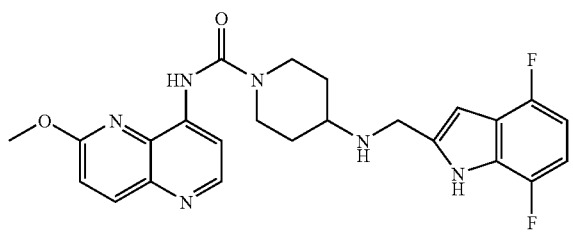

(a) 4-Amino-6-methoxy-[1,5]naphthyridine

A solution of 1,1,1-trifluoro-methanesulfonic acid 6-methoxy-[1,5]naphthyridin-4-yl carboxylic acid ester (8.0 g) [prepared as described in Example (18c)] and propylamine hydrochloride (15.8 g) in pyridine (120 ml) was heated at reflux for 4 hours. The solvent was evaporated and the mixture dissolved in 0.05M hydrochloric acid (600 ml) and washed with dichloromethane. The mixture was basified with 40% sodium hydroxide and extracted with dichloromethane. The extracts were dried, evaporated and chromatographed on silica gel (2-5% methanol in dichloromethane) to give an orange solid (3.6 g, 63%).

$^1$H NMR (CDCl$_3$) δ: 4.05 (3H,s), 5.25 (2H, brs), 6.71 (1H, d, J=5 Hz), 7.08 (1H, d, J=9 Hz), 8.09 (1H, d, J=9 Hz), 8.39 (1H, d, J=5 Hz).

MS (+ve ion electrospray) m/z: 176 (MH$^+$).

(b) 4-tert-Butoxycarbonylamino-1-(6-methoxy-[1,5]naphthyridin-4-yl)aminocarbonylpiperidine To a solution of 4-amino-6-methoxy-[1,5]naphthyridine (Example 400a) (2.1 g, 13.5 mmol) and 4-(dimethylamino)pyridine (1.62 g) in anhydrous chloroform (45 ml) was added N,N-carbonyldiimidazole (3.28 g, 20.1 mmol). The mixture was stirred for 4 h at room temperature, then evaporated and the residue was dissolved in anhydrous DMF (45 ml). 4-tert-Butoxycarbonylaminopiperidine hydrochloride (3.34 g, 13.5 mmol) and potassium carbonate (1.89 g) were added, and the mixture was heated at 70° C. overnight. The mixture was evaporated and the residue was mixed with water (120 ml). The solid was filtered off and dried (3.89 g).

MS (+ve ion electrospray) m/z 402 (MH+).

(c) 4-Amino-1-(6-methoxy-[1,5]naphthyridin-4-yl)aminocarbonylpiperidine

The tert-butoxycarbonylamino compound (400 b)(3.88 g, 9.7 mmol) was treated with trifluoroacetic acid and hydrogen chloride (4M in dioxan) as described in Example (1d). The crude hydrochloride was dissolved in water and washed twice with dichloromethane, basified to pH9 and evaporated to dryness. Extraction with 10% methanol/dichloromethane gave the free base (3.45 g).

MS (+ve ion electrospray) m/z 302 (MH+).

(d) Title Compound

A mixture of amine (400c)(0.10 g) and 4,7-fluoro-1H-indole-2-carboxaldehyde (150f) (0.06 g) and 3A molecular sieves in dichloromethane (4 ml) and methanol (4 ml) was stirred at room temperature for 6 hours, sodium borohydride (0.020 g) was added and the mixture was stirred for a further 24 hours. It was quenched with water and the organic layer separated, dried, evaporated and chromatographed on silica gel (2% methanol/dichloromethane) to afford a solid (0.062 g).

MS (+ve ion electrospray) m/z 467 (MH+)

$^1$H NMR (CDCl$_3$) δ:1.45 (2H, m), 1.75 (2H broad s), 2.05 (2H, broad d), 2.82 (1H, m), 3.12 (2H, t), 4.02 (3H, s), 4.05 (2H, s), 4.18 (2H, broad d), 6.45 (1H, broad s), 6.70 (2H, m), 7.12 (1H, d), 8.24 (1H, d), 8.30 (1H, d), 8.68 (1H, d), 9.08 (2H, broad s).

This was converted to the oxalate salt by the method of Example 16.

The following Examples were prepared by analogous methods

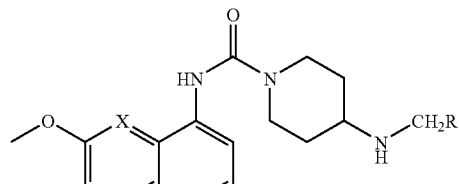

| Example | Method of synthesis | salt G oxalate S mesylate | X | R |
|---|---|---|---|---|
| 401 | A | G | N | 1H-indol-2-yl |
| 402 | A | S | N | quinoxalin-2-yl |
| 404 | A | G | N | 1H-pyrrolo[2,3-b]pyridin-2-yl |
| 405 | A | G | N | isoquinolin-3-yl |
| 407 | B | G | CH | 3-(R)-2,3-dihydro-[1,4]dioxino[2,3-b]pyridin-3-yl |
| 408 | C | G | N | 4-fluoro-1H-benzimidazol-2-yl |
| 409 | A | G | N | 8-hydroxyquinolin-2-yl |
| 410 | D | G | N | benzothiazol-2-yl |
| 411 | A | G | N | 8-hydroxyquinoxalin-2-yl |
| 412 | A | G | N | cinnolin-3-yl |
| 413 | A | G | N | benzo[1,2,5]thiadiazol-5-yl |
| 414 | A | G | N | 5-hydroxyquinoxalin-2-yl |

A by method of Example 400
B by method of Example (406a) and then Example 400
C by method of Example 403
D by method of Example (400a–c) and then Example 25

Example 403

4-[(4,6-Difluoro-1H-benzimidazol-2-ylmethyl)-amino]-piperidine-1-carboxylic acid (6-methoxy-[1,5]naphthyridin-4-yl)-amide, oxalate

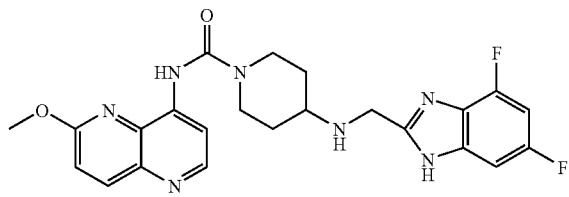

(a) 4-Oxo-1-(6-methoxy-[1,5]naphthyridin-4-yl)aminocarbonylpiperidine, ethylene ketal A solution of 4-amino-6-methoxy-[1,5]naphthyridine (400a) (0.32 g, 2 mmol) in chloroform (6 ml) was treated with N,N-dimethylaminopyridine (0.24 g, 2 mmol) then 1,1'-carbonyldiimidazole (0.42 g, 2.6 mmol). After 2 hours the chloroform was removed by evaporation and the residue treated with a solution of 4-oxopiperidine, ethylene ketal (0.31 g, 0.22 mmol) in N,N-dimethylformamide (5 ml). The mixture was heated at 100° C. for 1 hour, then partitioned between ethyl acetate and dilute brine. The organic extract was washed with water (3×), brine, dried and evaporated to give a yellow solid (0.8 g). Chromatography on silica gave the product as a white solid (0.47 g, 71%).

MS (+ve ion electrospray) m/z 345 (MH+).

(b) 4-Oxo-1-(6-methoxy-[1,5]naphthyridin-4-yl)aminocarbonylpiperidine

A solution of Example (403a) (0.46 g, 1.4 mmol) in acetone (25 ml) and water (5 ml) was treated with concentrated hydrochloric acid (0.2 ml) and the mixture heated to reflux for 4 hours. The cooled mixture was partitioned between ethyl acetate and saturated aqueous sodium bicarbonate solution. The organic extract was dried and evaporated to give a white solid (0.4 g). Chromatography gave the title compound (0.2 g, 46%).

MS (+ve ion electrospray) m/z 301 (MH+).

(c) Title Compound

This was prepared from ketone (403b)(0.08 g) and (4,6-difluoro-1H-benzimidazol-2-yl)-methylamine (12a) (0.049 g) by the method of Example (7c) to give a solid (0.046 g).

MS (+ve ion electrospray) m/z 468 (MH+).

This was converted to the oxalate salt by the method of Example 16.

Example 406

4-[(1H-Indol-2-ylmethyl)-amino]-piperidine-1-carboxylic acid (6-methoxy-quinolin-4-yl)amide, oxalate

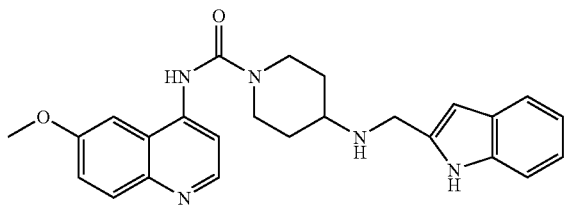

(a) 4-Amino-6-methoxyquinoline

Curtius rearrangement of 6-methoxyquinoline-4-carboxylic acid (1a) (4 g, 20 mmol) with diphenylphosphoryl azide (4.3 ml, 20 mmol) and triethylamine (3.5 ml) in tert-butanol (25 ml) at 85° C. gave, after chromatography (silica gel, ethyl acetate-dichloromethane) the N-tert-butoxycarbamate (2.47 g). Treatment with aqueous hydrochloric acid at reflux, followed by basification and extraction with ethyl acetate gave 4-amino-6-methoxyquinoline (0.74 g).

This compound may also be prepared from 4-hydroxy-6-methoxyquinoline by chlorination with phosphorus oxychloride, to give the 4-chloroquinoline, followed by treatment with n-propylamine hydrochloride by the method of Example (400a).

(b) 4-(1-Imidazolylcarbonyl)amino-6-methoxyquinoline

A suspension of 4-amino-6-methoxyquinoline (406a) (2.0 g, 11 mmol) in ethanol-free chloroform (60 ml) was treated with 4-N,N-dimethylaminopyridine (1.4 g, 11.4 mmol) and 1,1'-carbonyldiimidazole (2.6 g, 15.9 mmol). The suspension became clear over 1 hour then precipitation occurred. After a further 2 hours, filtration afforded the product as a white solid which was dried in vacuo (1.8 g, 59%).

(c) 4-tert-Butoxycarbonylamino-1-(6-methoxyquinolin-4-yl)aminocarbonylpiperidine The imidazolylcarbonyl compound (406b) (0.268 g, 1 mmol), 4-tert-butoxycarbonylaminopiperidine hydrochloride (0.24 g, 1 mmol) and potassium carbonate (0.14 g) were heated in DMF (2 ml) at 70° C. for 12 h. The mixture was evaporated and the residue was dissolved in ethyl acetate, washed with water and brine, dried and evaporated. The crude product was chromatographed on silica gel eluted with 0-4% methanol/dichloromethane to give the pure product (0.28 g).

MS (+ve ion electrospray) m/z 401 (MH+).

(d) 4-Amino-1-(6-methoxyquinolin-4-yl)aminocarbonylpiperidine

The tert-butoxycarbonylamino compound (406c) (0.275 g, 0.69 mmol) was treated with trifluoroacetic acid and hydrogen chloride as in Example (1d). The crude hydrochloride was dissolved in water, basified (pH 8-9) and evaporated, and the residue was extracted with 10% methanol/dichloromethane to give the free base (0.23 g).

MS (+ve ion electrospray) m/z 301 (MH+).

(e) Title Compound

This was prepared from amine (406d) (0.065 g) and 1H-indole-2-carboxaldehyde (0.032 g) by the method of Example (400d) to afford the free base (0.028 g).

MS (+ve ion electrospray) m/z 430 (MH+).

This was converted to the oxalate salt by the method of Example 16.

Example 600

7-Nitro-1H-indole-2-carboxylic acid {1-[(R)-2-hydroxy-2-(6-methoxy-quinolin-4-yl)-ethyl]-piperidin-4-yl}-amide mesylate

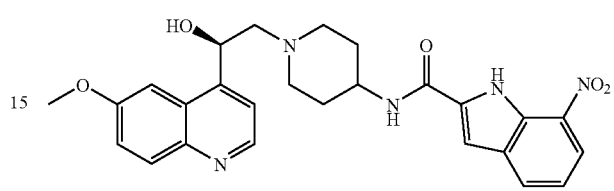

7-Nitro-1H-indole-2-carboxylic acid (34 mg) in dimethylformamide (0.4 ml) was treated with was O-(7-azabenzotriazol-1-yl)-N,N,N',N'-tetramethyluronium hexafluorophosphate (63 mg), diisopropylethylamine (0.03 ml, and amine (1d) and the mixture was agitated at room temperature for 4 hours. It was partitioned between dichloromethane and sodium bicarbonate solution and the organic layer was evaporated and purified on silica gel using a methanol-ethyl acetate gradient to give the free base of the title compound (29 mg) as a foam.

MS (+ve ion electrospray) m/z 490 (MH+)

$^1$H NMR (CDCl$_3$): δ:1.70 (6H, m), 2.10-2.65 (4H, m), 2.90 (2H, m), 3.35 (1H, br.d), 3.95 (3H, s), 5.50 (1H, m), 6.20 (1H, br.d), 7.00 (1H, s), 7.20 (1H, s), 7.25 (1H, m), 7.38 (1H, dd), 7.65 (1H, d), 7.95 (1H, d), 8.10 (1H, d), 8.30 (1H, d), 8.80 (1H, d).

This was converted to the mesylate salt by treatment with methane sulfonic acid in ether.

The following compounds were prepared by an analogous method to Example 600

| Example | salt<br>G oxalate<br>S mesylate<br>B dihydrochloride | X | R |
|---|---|---|---|
| 601 | S | CH | benzo[1,2,5]thiadiazol-5-yl |
| 602 | S | CH | 4,6-difluoro-1H-indol-2-yl |
| 603 | G | N$^\alpha$ | benzofuran-2-yl |
| 604 | S | CH | benzofuran-2-yl |
| 605 | S | CH | benzo[1,2,3]thiadiazol-5-yl |
| 606 | B | CH | 1H-pyrrolo[2,3-b]pyridin-2-yl |
| 607 | S | CH | 1H-indol-2-yl |
| 608 | S | CH | quinolin-3-yl |
| 609 | S | CH | benzothiazol-6-yl |
| 610 | S | CH | 1H-indol-6-yl |
| 611 | — | CH | 5-trifluoromethyl-thieno[3,2-b]pyridin-6-yl |
| 612 | — | CH | benzothiophen-2-yl |
| 613 | — | CH | 8-hydroxyquinolin-2-yl |
| 614 | — | CH | thieno[3,2-b]thiophen-2-yl |
| 615 | — | CH | 2-(1-phenyl-methanoyl)-1,2,3,4-tetrahydro- |

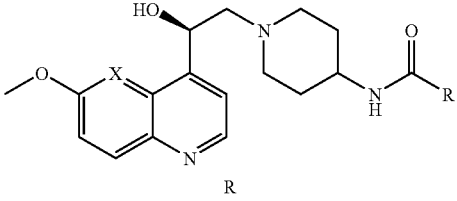

| Example | salt<br>G oxalate<br>S mesylate<br>B dihydrochloride | X | R |
|---|---|---|---|
| 616 | — | CH | isoquinolin-3-yl<br>4-dimethylsulfamoyl-1-methoxy-naphthalen-2-yl |

<sup>a</sup>amine (18f) used in place of amine (1d)

Example 620

4-[(5-Hydroxy-quinoxalin-2-ylmethyl)amino]-piperidine-1-carboxylic acid (5,8-difluoro-6-methoxy-quinolin-4-yl)-amide oxalate

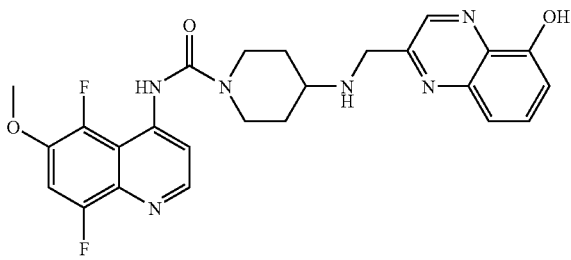

(a) 1,5-Difluoro-4-methoxy-phenylamine 1,2,4-Trifluoro-5-nitrobenzene (10 g, 56.5 mmol) was dissolved in methanol, cooled in ice and treated with 25% sodium methoxide in methanol. After being stirred at room temperature for 6 hours the mixture was diluted with water and extracted with ethyl acetate to give 1,4-difluoro-2-methoxy-5-nitrobenzene (10.1 g). This was dissolved in ethanol (400 ml) and hydrogenated over 10% palladium on carbon to give the title compound (7.8 g).

(b) 1,1,1-Trifluoro-methanesulfonic acid 5,8-difluoro-6-methoxy-quinolin-4-yl ester 5,8-Difluoro-6-methoxyquinolin-4-ol was prepared from the amine (620a) (7.8 g) by the method of Example (26a) (1.41 g) and was converted to the title compound by the method of Example (26b). Purification on silica gel (dichloromethane) afforded a yellow solid (0.76 g).

(c) 4-Amino-piperidine-1-carboxylic acid (5,8-difluoro-6-methoxy-quinolin-4-yl)-amide This was prepared (43%) as a yellow solid from the triflate (620b) by the method of Example (150a-d).

(d) Title Compound

This was prepared from amine (620c) (0.11 g) and 5-hydroxy-quinoxalin-2-carboxaldehyde [prepared from 5-hydroxy-2-methylquinoxaline (Y. Abe et al, *J. Med. Chem.* 41, 4062 (1998)) by oxidation with selenium dioxide in ethyl acetate (see Example 18a)] (0.057 g) by the method of Example (150 g). Purification on silica gel (5-10% methanol/dichloromethane) afforded the free base of the title compound (0.059 g).

$^1$H NMR (CDCl$_3$) δ: 1.54 (m), 1.76 (broad s), 2.08 (m), 2.90 (m), 3.12 (m), 4.02 (s), 4.10 (m), 4.24 (s), 7.25 (m), 7.63 (m), 8.45 (d), 8.57 (broad d), 8.67 (d), 8.77 (s).

MS (+ve ion electrospray) m/z 495 (MH+).

This was converted to the oxalate salt by the method of Example 16.

Example 621

4-[(8-Hydroxy-quinoxalin-2-ylmethyl)-amino]-piperidine-1-carboxylic acid (5,8-difluoro-6-methoxy-quinolin-4-yl)-amide oxalate

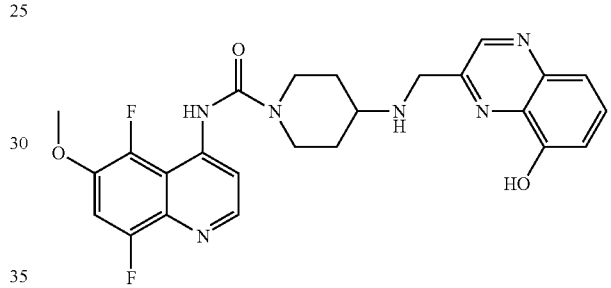

This was prepared from amine (620d) (0.05 g) and 8-hydroxy-quinoxalin-2-carboxaldehyde [prepared from 8-hydroxy-2-methylquinoxaline (Y. Abe et al, *J. Med. Chem.* 41, 4062 (1998)) by oxidation with selenium dioxide in ethyl acetate (see Example 18a)] (0.025 g) by the method of Example (150g). Purification on silica gel (5-10% methanol/dichloromethane) afforded the title compound (0.027 g)

$^1$H NMR (CDCl$_3$) δ: 1.51(m), 2.08(m), 2.89(m), 3.11(m), 4.01(s), 4.11(m), 4.25(s), 7.26(m), 7.66(m), 8.44(d), 8.56 (broad d), 8.67(d), 8.96(s).

MS (+ve ion electrospray) m/z 495 (MH+).

This was converted to the oxalate salt by the method of Example 16.

Example 622

(R)-2-{4-[(8-Hydroxy-1-oxo-1,2-dihydro-isoquinolin-3-ylmethyl)-amino]-piperidin-1-yl}-1-(6-methoxyquinolin-4-yl)-ethanol trihydrochloride

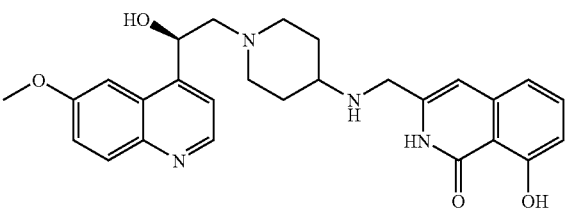

(a) Ethyl 2-methoxymethoxy-6-methylbenzoic acid

A solution of ethyl 2-hydroxy-6-methylbenzoic acid (4.56 g, 25.3 mmol) and diisopropylethylamine (13.2 ml, 76 mmol) in dry dichloromethane (30 ml) was cooled in an ice-bath. Chloromethyl methyl ether (3.83 ml, 50.6 mmol) was added slowly and the mixture was allowed stand at 0° C., warming slowly to room temperature. After 36 h a further portion of chloromethyl methyl ether (1.9 ml) was added and the mixture was left at room temperature overnight. The mixture was then washed with 10% citric acid, water and brine, dried and evaporated to give the title compound (6.34 g, 100%).

MS (+ve ion electrospray) m/z 225 (MH+).

(b) 8-Methoxymethoxy-1-oxo-1H-isochromene-3-carboxylic acid ethyl ester n-Butyllithium (1.6M in hexanes, 16.0 ml, 25.5 mmol) was added to a solution of diisopropylamine (3.64 ml, 25.5 mmol) and N,N,N',N'-tetramethylethylenediamine (4.01 ml, 25.5 mmol) in dry THF (36 ml) at −78° C. After 10 min a solution of the ester (622a) (5.10 g, 22.8 mmol) in dry THF (18 ml) was added dropwise, keeping internal temp.<−60° C. The deep red solution was stirred at −78° C. for 40 minutes, then diethyl oxalate (3.10 ml, 22.8 mmol) in THF (18 ml) was added over 5 minutes. The mixture was stirred at −78° C. for 6.5 hours, then treated with 10% citric acid. After warming to room temperature the phases were separated and the aqueous phase was extracted with ethyl acetate. The combined organics were washed with brine, dried and evaporated. Chromatography on silica gel (20-40% ethyl acetate/hexane) gave the title compound (2.05 g, 32%).

MS (+ve ion electrospray) m/z 235 (loss of methoxymethyl from MH+).

(c) 8-Methoxymethoxy-1,2-dihydro-1-oxo-isoquinoline-3-carboxylic acid ethyl ester The isochromene (622b) (2.04 g, 7.34 mmol) was heated under reflux with ammonium acetate (4.99 g) in ethanol (200 ml) for 24 hours. Solvent was evaporated and the residue was dissolved in ethyl acetate and water. The aqueous phase was extracted with ethyl acetate and combined organics were washed with water, dried and evaporated. Chromatography on silica gel (50-100% ethyl acetate/hexane) gave impure product and recovered isochromene. The latter was treated again with ammonium acetate (1.3 g) in refluxing ethanol (50 ml) for 48 hours, then worked up as before. The crude material was combined with the initial impure product for chromatography on silica gel (0-2% methanol/dichloromethane). Eluted material was rechromatographed (50-100% ethyl acetate/hexane) to give the title compound (0.87 g, 42%).

MS (+ve ion electrospray) m/z 278 (MH+).

(d) 8-Hydroxy-3-hydroxymethyl-2H-isoquinolin-1-one

The ester (622c) (0.66 g, 2.38 mmol) and sodium borohydride (0.14 g, 3.6 mmol) were heated in refluxing t-butanol (3 ml) while methanol (0.6 ml) was added over 1 hour. Heating was continued for 2 hours, then the cooled mixture was partitioned between ethyl acetate and water. The aqueous phase was re-extracted with ethyl acetate and the combined organics were washed with brine, dried and evaporated to give the title compound (0.51 g, 91%).

MS (+ve ion electrospray) m/z 236 (MH+).

(e) 8-Methoxymethoxy-1,2-dihydro-1-oxo-isoquinoline-3-carboxaldehyde

The alcohol (622d, 0.51 g, 2.17 mol) was stirred with manganese (IV) oxide (3.12 g) in 1:1 dichloromethane/THF (40 ml) at room temperature for 5 hours. The mixture was filtered and evaporated to give the aldehyde (0.32 g, 63%).

MS (−ve ion electrospray) m/z 232 (M−H⁻).

(f) (R)-2-{4-[(8-Methoxymethoxy-1-oxo-1,2-dihydro-isoquinolin-3-ylmethyl)-amino]-piperidin-1-yl}-1-(6-methoxyquinolin-4-yl)-ethanol The aldehyde (622e) (0.0.80 g, 0.34 mol) and 4-amino-1-[2-(R)-hydroxy-2-(6-methoxyquinolin-4-yl)]ethylpiperidine (1d) (0.105 g, 0.35 mmol) were stirred with 3A molecular sieves in dry dichloromethane (2 ml) and methanol (2 ml) overnight. Sodium borohydride (0.02 g) was added and the mixture was stirred at room temperature overnight. After two further additions of sodium borohydride (0.02 g each) the mixture was stirred overnight again. Water and dichloromethane were added, phases were separated and the aqueous phase was extracted with dichloromethane. Combined organics were washed with water, dried and evaporated. Chromatography on silica gel (2-10% methanol/dichloromethane) gave the title compound (0.064 g, 35%).

MS (+ve ion electrospray) m/z 519 (MH+).

(g) Title Compound

The methoxymethyl compound (622f) (0.097 g, 0.19 mmol) was partially dissolved in 5M hydrochloric acid (5 ml) and 1,4-dioxane (5 ml) and stirred at room temperature for 4 hours. Evaporation to dryness gave the title compound (0.105 g, 95%).

δH (d6-DMSO, 250 MHz), 2.24 (2H, m), 2.39 (2H, m), 3.1-3.5 (5H, m), 3.83 (1H, m), 4.11 (4H,s), 4.20 (2H, s), 6.38 (1H, d), 6.86 (1H, d), 6.94(1H, s), 7.09 (1H, d), 7.62 (1H, t), 7.76 (1H, dd), 7.83 (1H, s), 8.05 (1H, d), 8.32(1H, d), 9.08 (1H, d)

MS (+ve ion electrospray) m/z: 475 (MH⁺).

Example 623

(R)-1-(6-Methoxy-quinolin-4-yl)-2-{4-[(thiazolo[5,4-b]pyridin-6-ylmethyl)amino]-piperidin-1-yl}-ethanol dioxalate

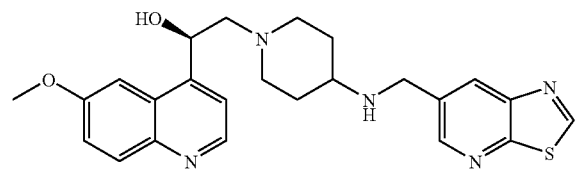

(a) 5-Amino-6-thioxo-1,6-dihydro-pyridine-3-carboxylic acid methyl ester

A mixture of sodium sulfide nonahydrate (2.17 g) and sulfur (0.29 g) was heated in boiling water (20 ml) until the solution was homogeneous and added to a solution of 6-chloro-5-nitro-nicotinic acid methyl ester [prepared as described by A. H. Berrie et al. J. Chem. Soc. 2590-2594 (1951)] (3.10 g) in methanol (50 ml). The mixture was boiled for 15 minutes and cooled. The resulting disulfide was collected and washed with water to give a yellow solid (2.46 g). The solid (5 g) in acetic acid (100 ml) and 4M HCl in dioxan (50 ml) was treated with zinc dust (12 g) and the mixture was stirred at room temperature for 30 minutes, filtered and evaporated to dryness. Sodium acetate and sodium sulfate were added and the mixture was extracted with warm chloroform and chromatographed on silica gel, eluting with chloroform then methanol-chloroform to afford a yellow solid (2.3 g).

MS (+ve ion electrospray) m/z 185(MH+)

(b) Thiazolo[5,4-b]pyridine-6-carboxylic acid methyl ester

The amine (623a) (0.7 g) was heated in formic acid (30 ml) under reflux for 30 minutes and was evaporated and chromatographed on silica gel (chloroform) to give a solid (0.65 g).

MS (+ve ion electrospray) m/z 195(MH+)

(c) Thiazolo[5,4-b]pyridin-6-yl-methanol

A solution of ester (623b) (200 mg) in dry tetrahydrofuran (5 ml) and dry ether (15 ml), cooled to −45° C., was treated with a 1M solution of lithium aluminium hydride in ether (1.55 ml) and the mixture was heated under reflux for 18 hours. It was cooled and a solution of saturated sodium carbonate was added cautiously. Dichloromethane and anhydrous sodium sulfate were added and the mixture was stirred for 15 minutes and filtered. The fitrate was evaporated to afford a white solid (95 mg).

MS (+ve ion electrospray) m/z 167(MH+)

(d) Thiazolo[5,4-b]pyridine-6-carboxaldehyde

The alcohol (623c) (65 mg) in chloroform (10 ml) was stirred with manganese dioxide (200 mg) for 5 hours, filtered and evaporated and chromatographed on silica gel, eluting with dichloromethane then chloroform, to give a solid (65 mg).

MS (+ve ion electrospray) m/z 165(MH+)

(e) Title Compound

A solution of the amine (1d; 94% ee) (81 mg) and carboxaldehyde (623d) (40 mg) in dichloromethane (3 ml) and methanol (3 ml) was treated with 3A molecular sieves and the mixture was heated at 50° C. for 4 hours. The mixture was cooled and treated with sodium borohydride (27 mg) and stirred at room temperature for 18 hours. It was filtered, evaporated to dryness, diluted with water, extracted with chloroform and chromatographed on silica gel (methanol-dichloromethane) to afford the free base of the title compound as an oil (40 mg).

δH (CDCl$_3$): 1.60 (2H, m), 2.10 (2H, br. t), 2.15-2.70 (4H, m), 2.80 (2H, dd), 3.30 (1H, br. d), 3.90 (3H, s), 4.05 (2H, s), 5.45 (1H, dd), 7.17 (1H, d) 7.35 (1H, dd), 7.66 (1H, d), 8.04 (1H, d), 8.38 (1H, s), 8.65 (1H, s), 8.75 (1H, d), 9.12 (1H, s).

MS (+ve ion electrospray) m/z 450 (MH$^+$).

The dioxalate salt was prepared by the same method as for Example 1.

Example 624

(R)-1-(6-Methoxy-quinolin-4-yl)-2-{4-[(1-carboxymethyl-1H-pyrrolo[2,3-b]pyridine-2-ylmethyl)-amino]-piperidin-1-yl}-ethanol trihydrochloride

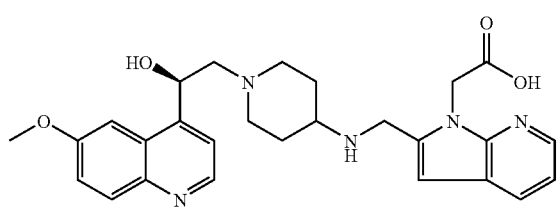

(a) (R)-1-(6-Methoxy-quinolin-4-yl)-2-{4-[(1-tert-butoxycarbonylmethyl-1H-pyrrolo[2,3-b]pyridine-2-ylmethyl)-amino]-piperidin-1-yl}-ethanol To a suspension of sodium hydride (60% in mineral oil, 0.02 g, 0.5 mmol) in dry THF at 0° C. was added (R)-1-(6-methoxy-quinolin-4-yl)-2-{4-[(1H-pyrrolo[2,3-b]pyridine-2-ylmethyl)-amino]-piperidin-1-yl}-ethanol (Example 17 free base) (0.20 g, 0.46 mmol). After stirring for 0.5 hours at 0° C., tert-butyl bromoacetate (0.081 ml, 0.5 mmol) was added. The mixture was stirred at room temperature overnight, then allowed to stand for another 48 hours. Solvent was evaporated and the residue was partitioned between dichloromethane/methanol and water. The organic phase was washed with water, dried and evaporated. Chromatography on silica gel (2-10% methanol/dichloromethane) gave the tert-butyl ester (0.053 g, 21%) as the first-eluted product.

MS (+ve ion electrospray) m/z: 546 (MH$^+$).

(b) Title Compound

The tert-butyl ester (624a, 0.053 g) was dissolved in aqueous hydrochloric acid (2.5M) and the solution was allowed to stand at room temperature for 11 hours. It was evaporated to dryness to give the title compound (0.058 g).

$^1$H NMR (CD$_3$OD) δ: 2.41 (2H, m), 2.60 (2H, m), 3.4-3.65 (4H, m), 3.85 (1H, m), 4.04 (1H, m), 4.19 (4H, s), 4.73 (2H, s), 5.44 (2H, s), 6.45 (1H, d), 7.27 (1H, s), 7.61 (1H, dd), 7.86 (2H, m), 8.23 (1H, d), 8.35 (1H, d), 8.52(1H, d), 8.66 (1H, d), 9.07 (1H, d).

MS (+ve ion electrospray) m/z 490 (MH+).

Example 625

(R)-1-(6-Methoxy-quinolin-4-yl)-2-{4-[carboxymethyl-(1-carboxymethyl-1H-pyrrolo[2,3-b]pyridine-2-ylmethyl)-amino]-piperidin-1-yl}-ethanol dihydrochloride

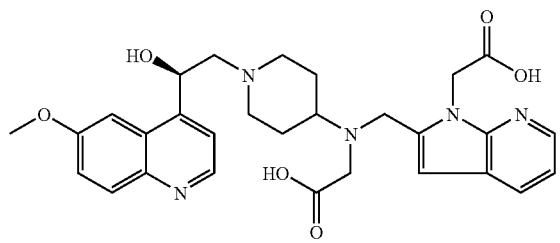

(a) (R)-1-(6-Methoxy-quinolin-4-yl)-2-{4-[tert-butoxycarbonylmethyl-(1-tert-butoxycarbonylmethyl-1H-pyrrolo[2,3-b]pyridine-2-ylmethyl)-amino]-piperidin-1-yl}-ethanol This compound was prepared as for Example 624a, the diester being the second eluted product from chromatography (0.063 g, 21%).

MS (+ve ion electrospray) m/z 660 (MH+).

(b) Title Compound

The di-tert-butyl ester (624a, 0.063 g) was dissolved in aqueous hydrochloric acid (2.5M) and the solution was allowed to stand at room temperature overnight. It was evaporated to dryness to give the title compound (0.058 g).

$^1$H NMR (CD$_3$OD) δ: 2.3-2.55 (4H, m), 3.35-3.65 (4H, m), 3.81 (1H, m), 4.00 (1H, m), 4.12 (2H,s), 4.18 (4H, s), 4.71 (2H, s), 5.75(2H, s), 6.45 (1H, d), 7.23 (1H, s), 7.69 (1H, t), 7.84 (1H, s), 7.86 (1H, d), 8.22 (1H, d), 8.33 (1H, d), 8.59 (1H, d), 8.78 (1H, d), 9.06 (1H, d).

MS (+ve ion electrospray) m/z 548 (MH+).

Biological Activity

The MIC (μg/ml) of test compounds against various organisms was determined: S. aureus Oxford, S. aureus WCUH29, S. pneumoniae 1629, S. pneumoniae N1387, S. pneumoniae ERY 2, E. faecalis 1, H. influenzae Q1, M. catarrhalis 1502. Examples 1-8, 11-13, 16-25, 50-63, 67, 71, 73, 74, 91-107, 150, 300-306, 308, 309, 400-402, 405, 407411, 601, 602, 604, 611-614, 622 have an MIC of less than or equal to 0.125 μg/ml; 10, 14, 15, 64-66, 68-70, 72, 75-85, 87, 108-113, 115-123, 150, 151, 170, 171, 307, 310, 312, 403, 404, 406, 412-414, 603, 605, 606-610, 623 have an MIC of less than or equal to 2 μg/ml; 9, 11, 86, 88-90, 114, 620, 624, 625 have an MIC less than or equal to 32 μg/ml against one or more of the above range of gram positive and gram negative bacteria.

The invention claimed is:
1. A compound which is:
(R)-2-{4-[(1H-Indol-2-ylmethyl)-amino]-piperidin-1-yl}-1-(6-methoxyquinolin-4-yl)-ethanol;
(R)-2-{4-[(Quinolin-2-ylmethyl)-amino]-piperidin-1-yl}-1-(6-methoxyquinolin-4-yl)-ethanol;
(R)-2-{4-[(Benzofuran-2-ylmethyl)-amino]-piperidin-1-yl}-1-(6-methoxyquinolin-4-yl)-ethanol;
(R)-2-{4-[(Quinolin-3-ylmethyl)-amino]-piperidin-1-yl}-1-(6-methoxyquinolin-4-yl)-ethanol;
(R)-2-{4-[(3-Chloro-benzothiophen-2-ylmethyl)-amino]-piperidin-1-yl}-1-(6-methoxyquinolin-4-yl)-ethanol;
(R)-2-{4-[(Benzofuran-2-ylmethyl)-amino]-4-hydroxymethyl-piperidin-1-yl}-1-(6-methoxyquinolin-4-yl)-ethanol;
(R)-2-{4-[(1H-Benzimidazol-2-ylmethyl)-amino]-piperidin-1-yl}-1-(6-methoxyquinolin-4-yl)-ethanol;
3-({1-[(R)-2-Hydroxy-2-(6-methoxyquinolin-4-yl)-ethyl]-piperidin-4-ylamino}-methyl)-chromen-4-one;
(R)-2-{4-[(5-Bromo-1H-indol-2-ylmethyl)-amino]-piperidin-1-yl}-1-(6-methoxy-quinolin-4-yl)-ethanol;
(R)-1-(6-Methoxy-quinolin-4-yl)-2-{4-[(1-methyl-1H-benzimidazol-2-ylmethyl)-amino]-piperidin-1-yl}-ethanol;
(R)-2-{4-[(6-Methoxy-benzothiazol-2-ylmethyl)-amino]-piperidin-1-yl}-1-(6-methoxy-quinolin-4-yl)-ethanol;
(R)-2-{4-[(4,6-Difluoro-1H-benzimidazol-2-ylmethyl)-amino]-piperidin-1-yl}-1-(6-methoxyquinolin-4-yl)-ethanol;
(R)-2-(4-[(4,5-Difluoro-1H-benzimidazol-2-ylmethyl)-amino]-piperidin-1-yl}-1-(6-methoxyquinolin-4-yl)-ethanol;
(R)-2-{4-[(5,6-Difluoro-1H-benzimidazol-2-ylmethyl)-amino]-piperidin-1-yl}-1-(6-methoxyquinolin-4-yl)-ethanol;
(R)-2-{4-[(5-Fluoro-1H-benzimidazol-2-ylmethyl)-amino]-piperidin-1-yl}-1-(6-methoxyquinolin-4-yl)-ethanol;
(R)-2-{4-[(4,6-Difluoro-1H-indol-2-ylmethyl)-amino]-piperidin-1-yl}-1-(6-methoxy-quinolin-4-yl)-ethanol;
(R)-1-(6-Methoxy-quinolin-4-yl)-2-{4-[(1H-pyrrolo[2,3-b]pyridine-2-ylmethyl)-amino]-piperidin-1-yl}-ethanol;
(R)-1-(6-Methoxy-[1,5]naphthyridin-4-yl)-2-{4-[(quinoxalin-2-ylmethyl)-amino]-piperidin-1-yl}-ethanol;
(R)-1-(6-Methoxy-quinolin-4-yl)-2-{4-[(1-H-pyrrolo[3,2-b]pyridin-2-ylmethyl)-amino]-piperidin-1-yl}-ethanol;
(R)-2-{4-[(Benzothiazol-2-ylmethyl)-amino]-piperidin-1-yl}-1-(6-methoxy-quinolin-4-yl)-ethanol;
1-{4-[(8-Hydroxy-quinolin-2-ylmethyl)-amino]-piperidin-1-yl}-2-(6-methoxy-quinolin-4-yl)-ethanone;
4-[(4,7-Difluoro-1-H-indol-2-ylmethyl)-amino]-piperidine-1-carboxylic acid (8-fluoro-6-methoxy-quinolin-4-yl)-amide;
4-[(4,6-Difluoro-1H-benzimidazol-2-ylmethyl)-amino]-piperidine-1-carboxylic acid (6-methoxy-[1,5]naphthyridin-4-yl)-amide;
4-[(1H-Indol-2-ylmethyl)-amino]-piperidine-1-carboxylic acid (6-methoxy-quinolin-4-yl)-amide;
7-Nitro-1H-indole-2-carboxylic acid {1-[(R)-2-hydroxy-2-(6-methoxy-quinolin-4-yl)-ethyl]-piperidin-4-yl}-amide;
4-[(5-Hydroxy-quinoxalin-2-ylmethyl)-amino]-piperidine-1-carboxylic acid (5,8-difluoro-6-methoxy-quinolin-4-yl)-amide;
4-[(8-Hydroxy-quinoxalin-2-ylmethyl)-amino]-piperidine-1-carboxylic acid (5,8-difluoro-6-methoxy-quinolin-4-yl)-amide;
(R)-2-{4-[(8-Hydroxy-1-oxo-1,2-dihydro-isoquinolin-3-ylmethyl)-amino]-piperidin-1-yl}-1-(6-methoxyquinolin-4-yl)-ethanol;
(R)-1-(6-Methoxy-quinolin-4-yl)-2-{4-[(thiazolo[5,4-b]pyridin-6-ylmethyl)-amino]-piperidin-1-yl}-ethanol;
(R)-1-(6-Methoxy-quinolin-4-yl)-2-{4-[(1-carboxymethyl-1H-pyrrolo[2,3-b]pyridine-2-ylmethyl)-amino]-piperidin-1-yl}-ethanol; or
(R)-1-(6-Methoxy-quinolin-4-yl)-2-{4-[carboxymethyl-(1-carboxymethyl-1H-pyrrolo[2,3-b]pyridine-2-ylmethyl)-amino]-piperidin-1-yl}-ethanol;
or a pharmaceutically acceptable salt thereof.

2. A pharmaceutical composition comprising a compound according to claim 1, and a pharmaceutically acceptable carrier.

3. A method of treatment of bacterial infections in mammals caused by S. aureus, S. pneumoniae, E. faecalis, H. influenzae, or M. catarrhalis which comprises the administration to a mammal in need of such a treatment an effective amount of a compound according to claim 1.

4. A compound which is:
a compound of formula (1):

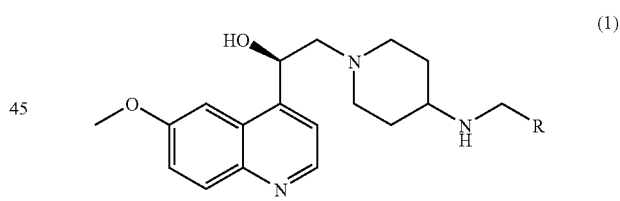

where R is:
4,7-difluoro-1H-indol-2-yl;
7-nitro-1H-indol-2-yl;
4-fluoro-1H-indol-2-yl;
4-chloro-1H-indol-2-yl;
2-Chloro-quinolin-3-yl;
3-methyl-benzofuran-2-yl;
5-fluoro-1H-indol-2-yl;
isoquinolin-3-yl;
2,3-dihydrobenzo[1,4]dioxin-2-yl;
benzo[b]thiophen-2-yl;
5-methylbenzothiophen-2-yl;
5,7-difluoro-1H-indol-2-yl;
benzoxazol-2-yl;
6-chloro-1H-indol-2-yl;
7-fluoro-3-methyl-3H-quinazolin-4-one-2-yl;
6-cyano-1H-indol-2-yl;

4,5-difluorobenzoxazol-2-yl;
5-nitro-1H-indol-2-yl;
imidazo[1,2-a]pyridin-2-yl;
3,6-dichloro-1H-indol-2-yl;
1H-indol-6-yl;
5-chloro-1H-indol-2-yl;
3H-quinazolin-4-one-2-yl;
6,7-difluoro-3H-quinazolin-4-one-2-yl;
7-methoxybenzofuran-2-yl;
5-fluoro-benzoxazol-2-yl;
5-methoxy-benzofuran-2-yl;
5-fluoro-3H-quinazolin-4-one-2-yl;
benzo[1,2,5]-oxadiazol-5-yl;
5-trifluoromethoxy-1H-indol-2-yl;
6-Fluoro-benzoxazol-2-yl;
oxazolo[4,5-b]-pyridin-2-yl;
3H-imidazo[4,5-b]-pyridin-2-yl;
6-fluoro-imidazo[1.2-a]pyridin-2-yl;
2-hydroxyquinolin-3-yl;
4-benzyloxy-1H-indol-2-yl;
4-hydroxy-1H-indol-2-yl;
7-methanesulphonyl-1H-indol-2-yl;
imidazo-[1,2-a]-pyrimidin-2-yl;
2-methyl[1,8]-naphthyridine-3-yl;
5-benzyloxy-1H-indol-2-yl;
3-fluoro-1H-indol-2-yl;
benzo[1,2,5]thiadiazol-5-yl;
3-(R)-(2,3-Dihydro-[1,4]dioxino[2,3-b]pyridin-3-yl;
8-hydroxyquinoxalin-2-yl;
cinnolin-3-yl;
6-Chloro-1H-pyrrolo[2,3-b]pyridin-2-yl;
5-hydroxyquinoxalin-2-yl;
pyrazolo[1,5-a]pyridin-2-yl;
3-fluoropyrazolo[1,5-a]pyridin-2-yl;
8-hydroxy-2H-isoquinolin-1-one-3-yl;
pyrido[1,2-a]pyrimidin-4-one-2-yl;
6-fluoropyrazolo[1,5-a]pyridin-2-yl;
4-nitro-1H-benzimidazol-2-yl;
4-fluoro-1H-benzimidazol-2-yl;
5-trifluoromethyl-thieno[3,2-b]pyridin-6-yl;
7-Fluoro-3-methyl-3H-quinazolin-4-one-2-yl;
imidazo[1,2-b]pyridazin-2-yl;
quinazolin-2-yl;
quinoxalin-6-yl;
7-fluoro-quinazolin-2-yl;
3-(R,S)-3,4-dihydro-2H-benzo[1,4]thiazin-3-yl;
7-benzyloxy-1H-indol-2-yl;
benzo[1,2,3]thiadiazol-6-yl;
thiazolo[3,2-a]pyrimidin-5-one-7-yl;
thiazolo[5,4-b]pyridin-2-yl;
pyrido[1.2-a]pyrimidin-4-one-3-yl;
1-isopropyl-1H-benzotriazol-5-yl;
4-cyano-1H-benzimidazol-2-yl;
6-chloro-imidazo[1,2-b]pyridazine-2-yl;
3H-benzothiazol-2-one-5-yl;
3-(S)-(2,3-dihydro-[1,4]dioxino[2,3-b]pyridin-3-yl; or
5-chloro-3H-benzooxazol-2-one-6-yl;

a compound of formula (2):

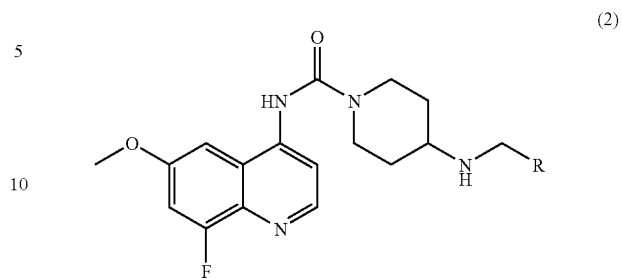

(2)

where R is 8-hydroxyquinoxalin-2-yl or 8-hydroxyquinolin-2-yl;

a compound of formula (3):

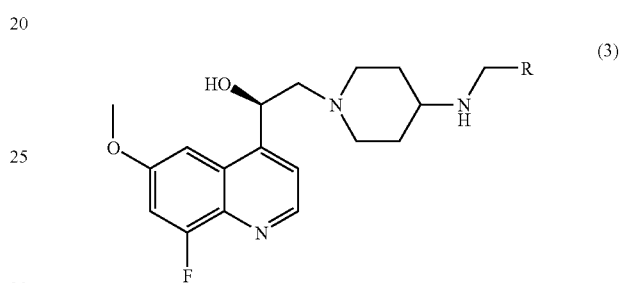

(3)

where R is 4-fluoro-1H-benzimidazol-2-yl or 3H-imidazo[4,5-b]pyridin-2-yl;

a compound of formula (4):

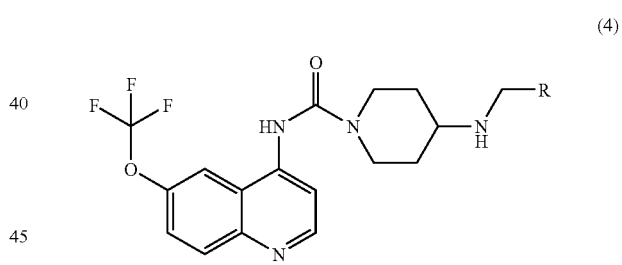

(4)

where R is 8-hydroxyquinoxalin-2-yl or 5-hydroxyquinoxalin-2-yl, a compound of formula (5):

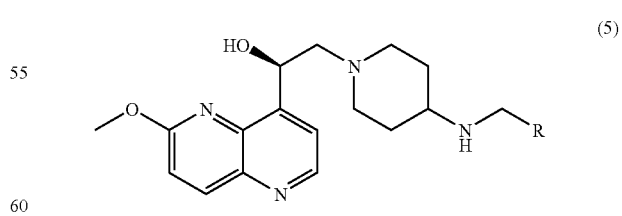

(5)

where R is:
4,7-difluoro-1H-indol-2-yl;
1H-indol-2-yl;
4,6-difluoro-1H-indol-2-yl;
isoquinolin-3-yl;

benzoxazol-2-yl;
1H-pyrrolo[2,3-b]pyridin-2-yl;
imidazo[1,2-a]pyridin-2-yl;
4-fluoro-1H-benzimidazol-2-yl;
3-(R)-(2,3-Dihydro-[1,4]dioxino[2,3-b]pyridin-3-yl;
3-(S)-(2,3-Dihydro-[1,4]dioxino[2,3-b]pyridin-3-yl;
benzo[1,2,3]thiadiazol-5-yl;
imidazo[1,2-a]pyridazin-2-yl;or
3-fluoropyrazolo[1,5-a]pyridin-2-yl;
a compound of formula (6):

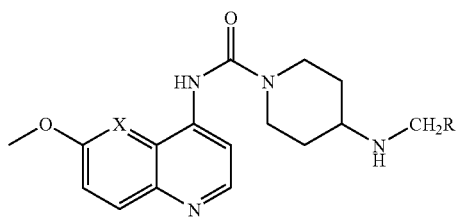
(6)

where X and R are:

| X | R |
|---|---|
| N | 1H-indol-2-yl; |
| N | quinoxalin-2-yl; |
| N | 1H-pyrrolo[2,3-b]pyridin-2-yl; |
| N | isoquinolin-3-yl; |
| CH | 3-(R)-2,3-dihydro-[1,4]dioxino[2,3-b]pyridin-3-yl; |
| N | 4-fluoro-1H-benzimidazol-2-yl; |
| N | 8-hydroxyquinolin-2-yl; |
| N | benzothiazol-2-yl; |
| N | 8-hydroxyquinoxalin-2-yl; |
| N | cinnolin-3-yl; |
| N | benzo[1,2,5]thiadiazol-5-yl; or |
| N | 5-hydroxyquinoxalin-2-yl; | or a compound of formula (7):

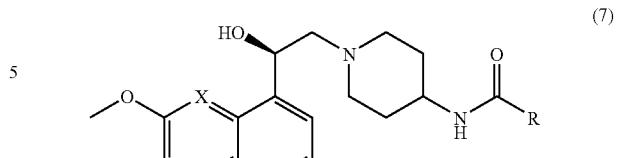
(7)

where X and R are:

| X | R |
|---|---|
| CH | benzo[1,2,5]thiadiazol-5-yl; |
| CH | 4,6-difluoro-1H-indol-2-yl; |
| N | benzofuran-2-yl; |
| CH | benzofuran-2-yl; |
| CH | benzo[1,2,3]thiadiazol-5-yl; |
| CH | 1H-pyrrolo[2,3-b]pyridin-2-yl; |
| CH | 1H-indol-2-yl; |
| CH | quinolin-3-yl; |
| CH | benzothiazol-6-yl; |
| CH | 1H-indol-6-yl; |
| CH | 5-trifluoromethyl-thieno[3,2-b]pyridin-6-yl; |
| CH | benzothiophen-2-yl; |
| CH | 8-hydroxyquinolin-2-yl; |
| CH | thieno[3,2-b]thiophen-2-yl; |
| CH | 2-(1-phenyl-methanoyl)-1,2,3,4-tetrahydro-isoquinolin-3-yl; or |
| CH | 4-dimethylsulfamoyl-1-methoxy-naphthalen-2-yl; | or a pharmaceutically acceptable salt thereof.

5. A pharmaceutical composition comprising a compound according to claim 4, and a pharmaceutically acceptable carrier.

6. A method of treatment of bacterial infections in mammals caused by *S. aureus, S. pneumoniae, E. faecalis, H. influenzae*, or *M. catarrhalis* which comprises the administration to amammal in need of such a treatment an effective amount of a compound according to claim 4.

\* \* \* \* \*